(12) United States Patent
Song et al.

(10) Patent No.: US 8,580,964 B2
(45) Date of Patent: Nov. 12, 2013

(54) CINCHONA-BASED BIFUCNTIONAL ORGANOCATALYSTS AND METHOD FOR PREPARING CHIRAL HEMIESTERS USING THE SAME

(75) Inventors: Choong Eui Song, Gyeonggi-do (KR); Sang Ho Oh, Gyeonggi-do (KR); Ho Sik Rho, Gyeonggi-do (KR); Ji Woong Lee, Seoul (KR); Je Wun Lee, Gyeonggi-do (KR); Sung Hoon Youk, Seoul (KR); Jik Chin, Ontario (CA)

(73) Assignee: Sungkyunkwan University Foundation for Corporate Collaboration, Suwon-si (KR)

( * ) Notice: Subject to any disclaimer, the term of this patent is extended or adjusted under 35 U.S.C. 154(b) by 209 days.

(21) Appl. No.: 13/008,793

(22) Filed: Jan. 18, 2011

(65) Prior Publication Data

US 2011/0213151 A1    Sep. 1, 2011

Related U.S. Application Data

(63) Continuation-in-part of application No. PCT/KR2008/006169, filed on Oct. 17, 2008.

(30) Foreign Application Priority Data

Jul. 18, 2008 (KR) ........................ 10-2008-0070007

(51) Int. Cl.
*C07D 453/04* (2006.01)
(52) U.S. Cl.
USPC ........................................................ 546/136
(58) Field of Classification Search
None
See application file for complete search history.

(56) References Cited

U.S. PATENT DOCUMENTS 6,580,003 B2   6/2003   Deng et al.

FOREIGN PATENT DOCUMENTS

| CN | 101029049 A | 9/2007 |
| KR | 10-0769381 B1 | 10/2007 |
| WO | WO 97/46557 A1 | 12/1997 |

OTHER PUBLICATIONS

Brunner et al., Asymmetric Catalysis, 152 Alpha-Amino Acid Derivatives by Enantioselective Decarboxylation, 15 Euro. J. Org. Chem. 2854-2862 (2003) (CAS Abstract).*
Bolm et al., "Practical and Highly Enantioselective Ring Opening of Cyclic Meso-Anhydrides Mediated by Cinchona Alkaloids", J. Org. Chem., vol. 65, No. 21, pp. 6984-6991, 2000.
Chen et a., "A Highly Enantioselective Catalytic Desymmetrization of Cyclic Anhydrides with Modified Cinchona Alkaloids" J. Amerian Chemical Society, vol. 122, No. 39, pp. 9542-9543, 2000.
Hiratake et al., "Enantiotopic-group Differentiation. Catalytic Asymmetric Ring-opening of Prochiral Cyclic Acid Anhydrides with Methanol, using Cinchona Alkaloids", J. Chem Soc. Perkin Trans. I, pp. 1053-1058, 1987.
International Search Report dated Apr. 10, 2009, issued in PCT/KR2008/006169.
Ishii et al., "Practical Syntheses of Chiral • -Amino Acids and Chiral Half-Esters by Kinetic Resolution of Urethane-Protected • -Amino Acid N-Carboxyanhydrides and Desymmetrization of Cyclic meso-Anhydrides with New Modified Cinchona Alkaloid Catalysts", Organic Process Research & Development, vol. 11, No. 3, pp. 609-615, 2007.
Peschiulli et al., "Highly Enantioselective Desymmetrization of Meso Anhydrides by a Bifunctional Thiourea-Based Organocatalyst at Low Catalyst Loadings and Room Temperature", J. Org. Chem., vol. 73, No. 6, pp. 2454-2457, 2008.
Rho et al., "Bifunctional organocatalyst for methanolytic desymmetrization of cyclic anhydrides: increasing enantioselectivity by catalyst dilution", Chem. Comm., pp. 1208-1210, 2008.
Song et al., "Silica gel-supported bis-cinchona alkaloid: a chiral catalyst for the heterogeneous asymmetric desymmetrization of meso-cyclic anhydrides", Tetrahedron Letters, vol. 45, pp. 3301-3304, 2004.
Vakulya et al., "Highly Enantioselective Conjugate Addition of Nitromethane to Chalcones Using Bifunctional Cinchona Organocatalysts", Organic Letters, vol. 7, No. 10, pp. 1967-1969, 2005.
Brunner et al., "a-Amino Acid Derivatives by Enantioselective Decarboxylation", Eur. J. Org. Chem., 2003, pp. 2854-2862.
Fillion et al., "Sequential Rh(I)/Pd-Catalyzed 1,4-Addition/Intramolecular Allylation: Stereocontrolled Construction of y-Butyrolactones and Cyclopropanes", Organic Letters, vol. 10, No. 3, 2008, pp. 437-440.
Japanese Office Action for corresponding Application No. 2011-518633 dated Feb. 26, 2013.
Mazurov et al., "2-(Arylmethyl)-3-substitiuted quinuclidines as selective a7 nicotinic receptor ligands", Bioorganic & Medicinal Chemistry Letters, vol. 15, 2005, pp. 2073-2077.
Oh et al., "A Highly Reactive and Enantioselective Bifunctional Organocatalyst for the Methanolytic Desymmetrization of Cyclic Anhydrides: Prevention of Catalyst Aggregation", Angew. Chem. Int. Ed., vol. 47, 2008, pp. 7872-7875.
Sundermeier et al., "Synthesis of 9-N-Cinchona Alkaloid Peptide Hybrid Derivatives: Preparation and Conformational Study of 9-N-Acylamino(9-deoxy)cinchona Alkaloids", Chirality, vol. 15, 2003, pp. 127-134.
Wu et al., "Synthesis of chiral sulfonamides derived from cinchonine", vol. 30, No. 3, 2008, pp. 213-214 (with English abstract).

* cited by examiner

*Primary Examiner* — Janet Andres
*Assistant Examiner* — Timothy R Rozof
(74) *Attorney, Agent, or Firm* — Birch, Stewart, Kolasch & Birch, LLP

(57) ABSTRACT

The present invention relates to cinchona-based bifunctional organocatalysts and methods for preparing chiral hemiesters using the same. More specifically, the present invention relates to methods for preparing chiral hemiesters from prochiral or meso cyclic acid anhydrides via desymmetrization, using bifunctional cinchona alkaloid catalysts comprising sulfonamide functional groups.

20 Claims, 4 Drawing Sheets

CINCHONA-BASED BIFUCNTIONAL ORGANOCATALYSTS AND METHOD FOR PREPARING CHIRAL HEMIESTERS USING THE SAME

The present application is a continuation-in-part of and claims priority to PCT/KR2008/006169 filed on Oct. 17, 2008, which claims priority to Korean Patent Application No. 2008-0070007, filed on Jul. 18, 2008, and all the benefits accruing therefrom under 35 U.S.C. §119, the content of which is incorporated herein by reference in its entirety.

TECHNICAL FIELD

The present invention relates to cinchona-based bifunctional organocatalysts and methods for preparing chiral hemiesters using the same. More specifically, the present invention relates to methods for preparing chiral hemiesters from prochiral or meso cyclic acid anhydrides via desymmetrization, using bifunctional cinchona alkaloid catalysts comprising sulfonamide functional groups.

BACKGROUND ART

Recently, enantiomerically pure compounds are taking on significance. Specifically in pharmaceutical industry, enantiomerically pure compounds often show low side effects and high titer over racemic compounds, and thus have very high availability. Conventional methods of organic synthesis for obtaining pure enantiomers use often chiral adjuvants, which can be obtained from natural products, or resolution of racemic compounds. The chiral adjuvants should be used in an equivalent amount rather than a catalytic amount, and are naturally occurring compounds, whereby they are structurally limited. The method of resolving racemates using resolving agents means that the undesired enantiomers are discarded, and has drawbacks of low yield and waste.

Oda, et al. (J. Oda, *J. Chem. Soc. Perkin Trans I.* 1987, 1053) reported a method for preparing chiral hemiesters comprising performing a ring-opening reaction of cyclic acid anhydrides using (+)-cinchonine, of cinchona alkaloids, in a catalytic amount (10 mol %). However, said method has problems that the reaction time is as long as 4 days and the enantioselectivity is low (up to 69% ee).

Bohn, et al. (C. Bolm, *J. Org. Chem.* 2000, 65, 6984) described an efficient method for preparing chiral hemiesters having the enantioselectivity of up to 91% ee comprising subjecting 10 mol % of qunidine to a ring-opening of cyclic acid anhydrides. But, there are problems that 1 equivalent of expensive pempidine must be used and that the reaction must be performed at −55° C. for up to 6 days.

Furthermore, L. Deng, et al. reported, in KR Patent No. 10-0769381, a method of using modified bis-cinchona alkaloids, for example, (DHQD)2AQN as a catalyst, among method for preparing chiral hemiesters using organocatalysts (Y. Chen, S.-K. Tian, L. Deng, *J. Am. Chem. Soc.* 2000, 122, 9542-9543). If said catalyst is used, the reaction may be successfully completed due to high enantioselectivity. However, there is a problem that it is industrially applied, since the very long reaction time (up to 140 hours) is required, the amount of the catalyst is relatively high, and the low temperature (−20° C. to −40° C.) must be maintained to obtain high enantioselectivity. Furthermore, a problem has been reported, in which quantity synthesis of catalyst is very difficult (Y. Ishii, et al., *Organic Process Research & Development*, 2007, 11, 609-615).

To obtain chiral hemesters having high enantioselectivity, the existing synthetic methods have a drawback that the reaction should be performed at low temperature for a long time. Therefore, it is required to develop more efficient catalysts and methods for preparing the same.

DISCLOSURE

Technical Problem

As the inventors analyzed the above techniques, they assumed as the main cause, which requires low temperature and long reaction time to obtain high enantioselectivity, that nitrogen atom of chiral tertiary amine, for example, quinuclidine, in the structure of cinchona alkaloid catalyst served as a monofunctional catalyst activating a nucleophile.

Therefore, the inventors designed and synthesized bifunctional catalysts, which may activate meso-cyclic acid anhydrides as starting materials, that is, may activate simultaneously an electrophile and a nucleophile, by modifying the structure of cinchona alkaloids. Then, on reacting a prochiral or meso-cyclic acid anhydride and an alcohol as nucleophiles, in an aprotic solvent comprising oxygen, in the presence of said derivatized bifunctional organo catalyst of cinchonal alkaloid, they found that chiral hemiesters having high enantioselectivity could be prepared at normal temperature within 1 to 10 hours, and completed the present invention.

Accordingly, one object of the present invention is to provide a derivatized bifunctional cinchona alkaloid catalyst.

Another object of the present invention is to provide a method for synthesizing said derivatized bifunctional cinchona alkaloid catalyst comprising a step of reacting an amine containing 1-azabicyclo[2.2.2]octane moiety with a sulfonyl derivative.

The other object of the present invention is to provide a method for preparing effectively a chiral hemiester by reacting a prochiral compound or a meso-cyclic acid anhydride in an organic solvent with a nucleophile in the presence of said derivatized bifunctional cinchona alkaloid catalyst.

Technical Solution

To achieve the objects as above, the present invention provides a compound of Formula 1 and its salt below:

[Formula 1]

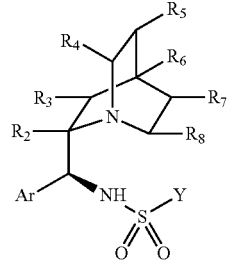

wherein,
Ar represents an aryl having 4 to 11 member ring,
$R_2$, $R_3$, $R_4$, $R_6$, $R_7$ and $R_8$ represent hydrogen,
$R_5$ represent an alkyl having 1 to 12 carbons, an alkenyl having 2 to 12 carbons, an alkynyl having 2 to 12 carbons, an alkoxy having 1 to 12 carbons or an aryl having 4 to 11 member ring, and Y represents an alkyl having 1 to 12 carbons, an alkenyl having 2 to 12 carbons, a cycloalkyl having 3 to 10 carbons, or an aryl having 4 to 11 member ring, with the proviso that Y is not para-toluene.

The present invention also provides a compound of Formula 2 and its salt below:

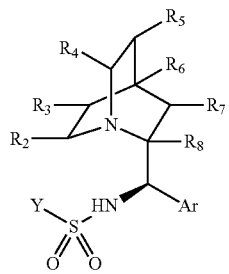

[Formula 2]

wherein,
Ar represents an aryl having 4 to 11 member ring,
$R_2$, $R_4$, $R_5$, $R_6$, $R_7$ and $R_8$ represent hydrogen,
$R_3$ represent an alkyl having 1 to 12 carbons, an alkenyl having 2 to 12 carbons, an alkynyl having 2 to 12 carbons, an alkoxy having 1 to 12 carbons or an aryl having 4 to 11 member ring, and
Y represents an alkyl having 1 to 12 carbons, an alkenyl having 2 to 12 carbons, a cycloalkyl having 3 to 10 carbons, or an aryl having 4 to 11 member ring, with the proviso that Y is not para-toluene.

The present invention also provides a method for preparing a chiral hemiester comprising a step of reacting a pro chiral compound or a meso-cyclic acid anhydride with a nucleophile in the presence of a compound of Formula I below:

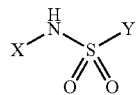

[Formula I]

wherein,
X represents an organic group containing 1-azabicyclo[2.2.2]octane moiety; and
Y represents alkyl, alkenyl, cycloalkyl, or aryl.

The compound of Formula I above is a compound of Formula 1 or 2 below:

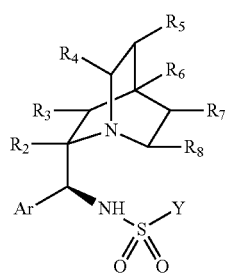

[Formula 1]

wherein,
Ar represents an aryl having 4 to 11 member ring,
$R_2$, $R_3$, $R_4$, $R_6$, $R_7$ and $R_8$ represent hydrogen, $R_5$ represent an alkyl having 1 to 12 carbons, an alkenyl having 2 to 12 carbons, an alkynyl having 2 to 12 carbons, an alkoxy having 1 to 12 carbons or an aryl having 4 to 11 member ring, and
Y represents an alkyl having 1 to 12 carbons, an alkenyl having 2 to 12 carbons, a cycloalkyl having 3 to 10 carbons, or an aryl having 4 to 11 member ring, with the proviso that Y is not para-toluene.

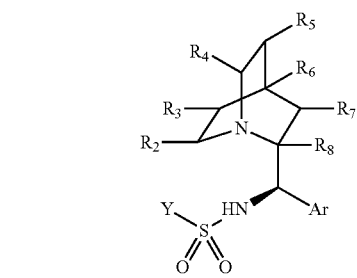

[Formula 2]

wherein,
Ar represents an aryl having 4 to 11 member ring,
$R_2$, $R_4$, $R_5$, $R_6$, $R_7$ and $R_8$ represent hydrogen,
$R_3$ represent an alkyl having 1 to 12 carbons, an alkenyl having 2 to 12 carbons, an alkynyl having 2 to 12 carbons, an alkoxy having 1 to 12 carbons or an aryl having 4 to 11 member ring, and
Y represents an alkyl having 1 to 12 carbons, an alkenyl having 2 to 12 carbons, a cycloalkyl having 3 to 10 carbons, or an aryl having 4 to 11 member ring, with the proviso that Y is not para-toluene.

The compound of Formula I above is a compound of Formula 1a or 2a below:

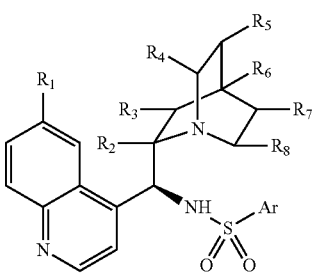

[Formula 1a]

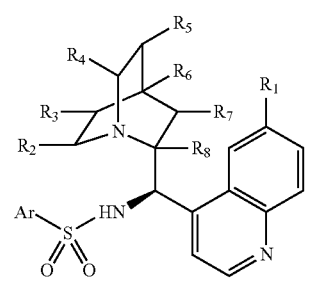

[Formula 2a]

wherein,
Ar represents an aryl group having 4 to 11 member ring, with the proviso that Ar is not para-toluene, and
$R_1$ represents hydrogen, an alkyl having 1 to 12 carbons, an alkenyl having 2 to 12 carbons, an alkynyl having 2 to 12 carbons, an alkoxy having 1 to 12 carbons, or an aryl having 6 to 11 member ring, $R_2$, $R_4$, $R_6$, $R_7$ and $R_8$ represent hydrogen, and One of $R_3$ and $R_5$ represent an alkyl having 1 to 12 carbons, an alkenyl having 2 to 12 carbons, an alkynyl having 2 to 12 carbons, an alkoxy having 1 to 12 carbons or an aryl having 4 to 11 member ring and the other one is hydrogen.

The compound of Formula I above is a compound of Formula 1b or 2b below:

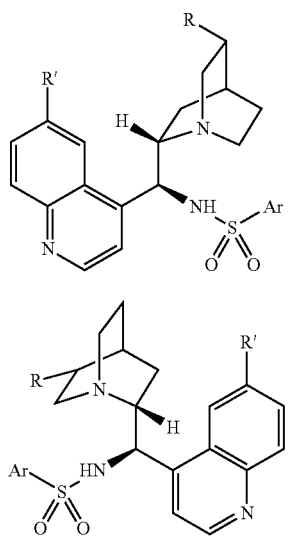

[Formula 1b]

[Formula 2b]

wherein,

R represents ethyl or —CH=CH$_2$;

R' represents H or OCH$_3$; and

Ar represents an aryl group having 4 to 11 member ring, with the proviso that Ar is not para-toluene.

The present invention also provides a method for preparing said compound of Formula 1 or 2 comprising a step of reacting an amine of Formula 3 or 4 below with a sulfonyl derivative of Formula 5 below:

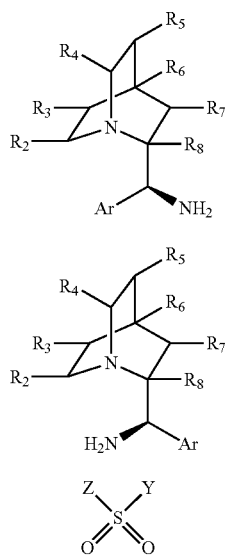

[Formula 3]

[Formula 4]

[Formula 5]

wherein,

Ar represents an aryl having 4 to 11 member ring, $R_2$, $R_4$, $R_6$, $R_7$ and $R_8$ represent hydrogen, One of $R_3$ and $R_5$ represent an alkyl having 1 to 12 carbons, an alkenyl having 2 to 12 carbons, an alkynyl having 2 to 12 carbons, an alkoxy having 1 to 12 carbons or an aryl having 4 to 11 member ring and the other one is hydrogen, Y represents an alkyl having 1 to 12 carbons, an alkenyl having 2 to 12 carbons, a cycloalkyl having 3 to 10 carbons, or an aryl having 4 to 11 member ring, with the proviso that Y is not para-toluene, and Z represents a halogen atom.

Advantageous Effects

The derivatized bifunctional cinchona alkaloid catalyst of the present invention may be synthesized from quinine, quinidine, hydroquinine, hydroquinidine, cinchonine, cinchonidine, hydrocinchonine or hydrocinchonidine which is easily obtainable from natural products, and has low toxicity and is chemically stable, other than metal catalysts, so that it has high industrial usefulness. In addition, it can proceed for the reaction to be performed in the atmosphere, has high enantioselectivity even at normal temperature, not at high or low temperature, and can be easily recovered after the reaction and reused.

According to the preparation method of the present invention, chiral hemiesters having various structures may be synthesized within a short time so as to have high enantioselectivity, by performing a ring-opening reaction of prochiral or meso-cyclic acid anhydrides with alcohols in an organic solvent at −20° C. to normal temperature in the presence of the bifunctional cinchona alkaloid catalyst derivatized by said sulfonamide moiety.

Those skilled in this technical field may recognize or identify most aspects equivalent to specific aspects described herein without any further experiment. It is considered that these equivalents are included in the following claims.

BEST MODE

Figure 1:
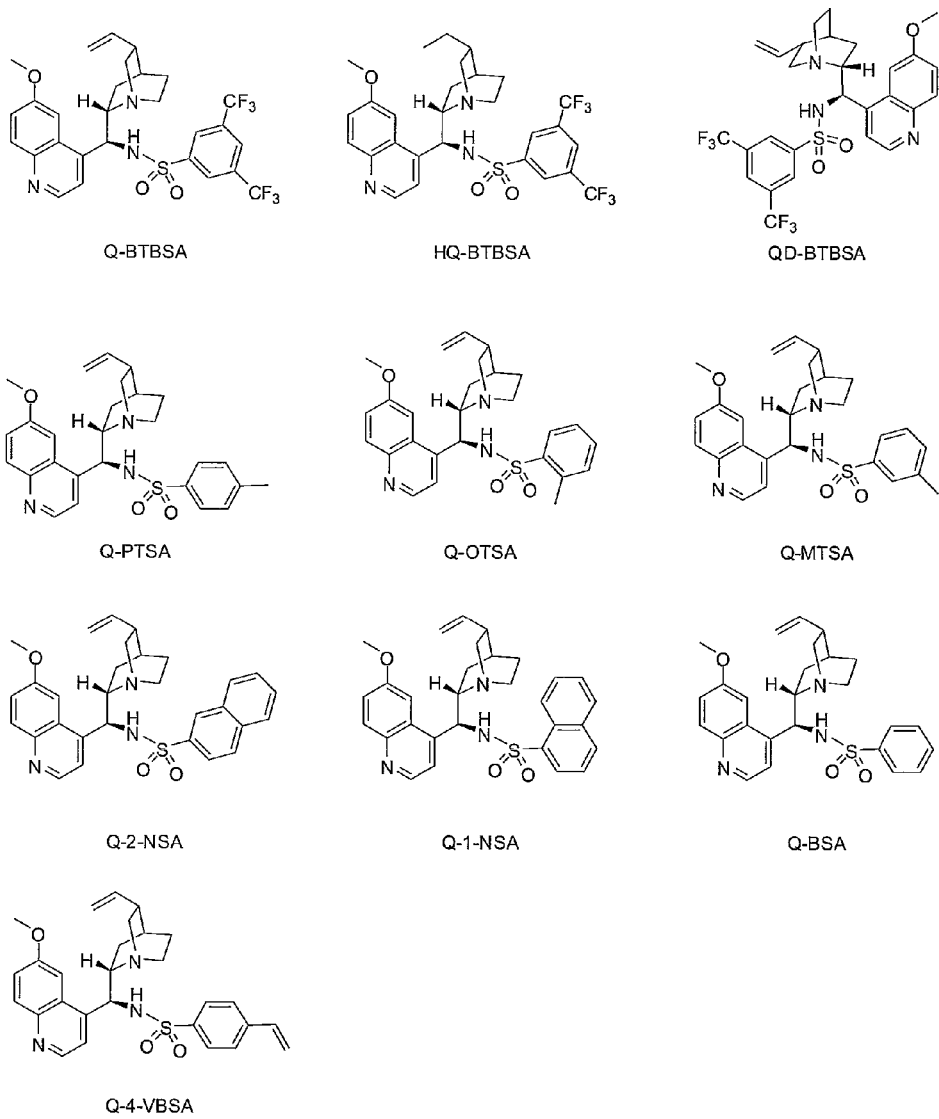
FIG. 1 shows structural formulas of bifunctional cinchona alkaloid catalysts of the present invention, such as Q-BTBSA, HQ-BTBSA, QD-BTBSA, Q-OTSA, Q-MT SA, Q-1-NSA and Q-2-NSA.
Figure 2:
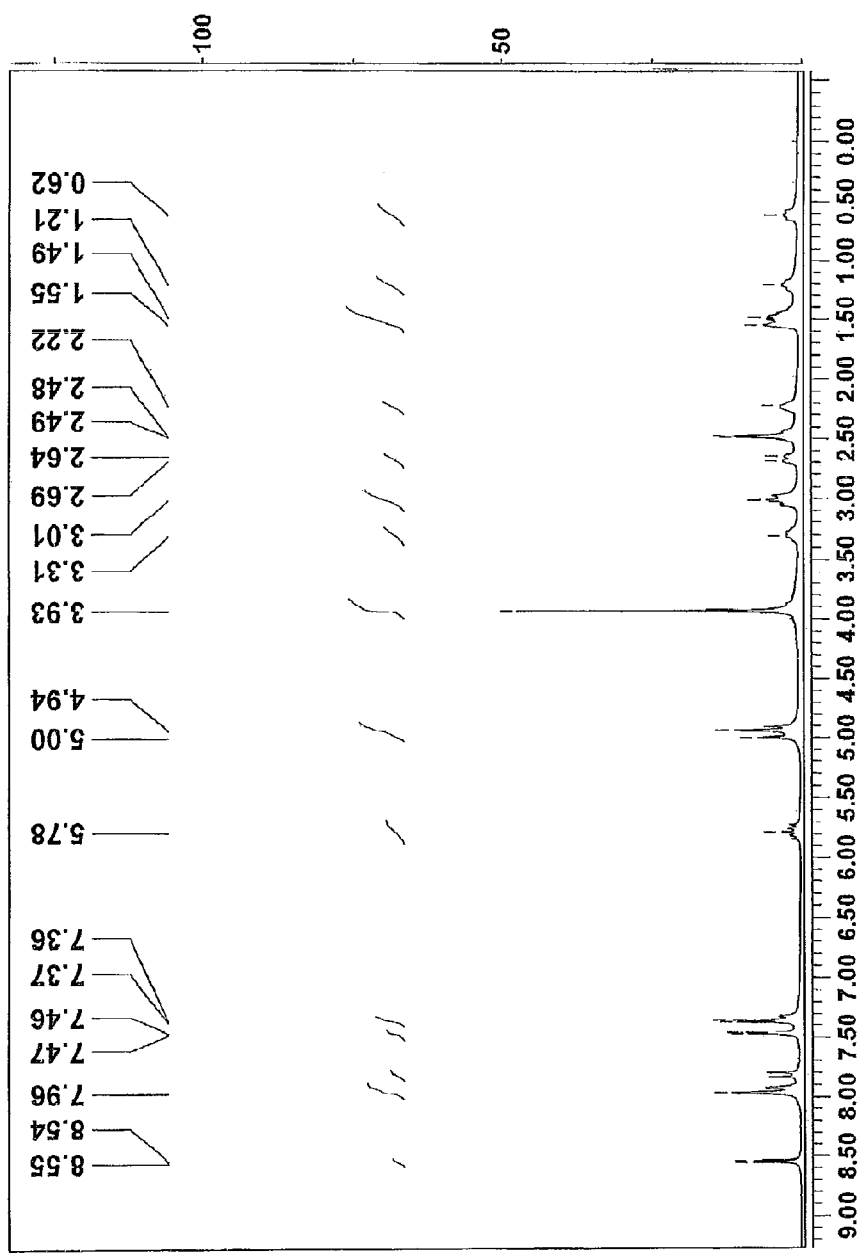
FIG. 2 shows $^1$H-NMR spectrum of the Q-BTBSA catalyst synthesized by using the present method described in Example 1.
Figure 3:
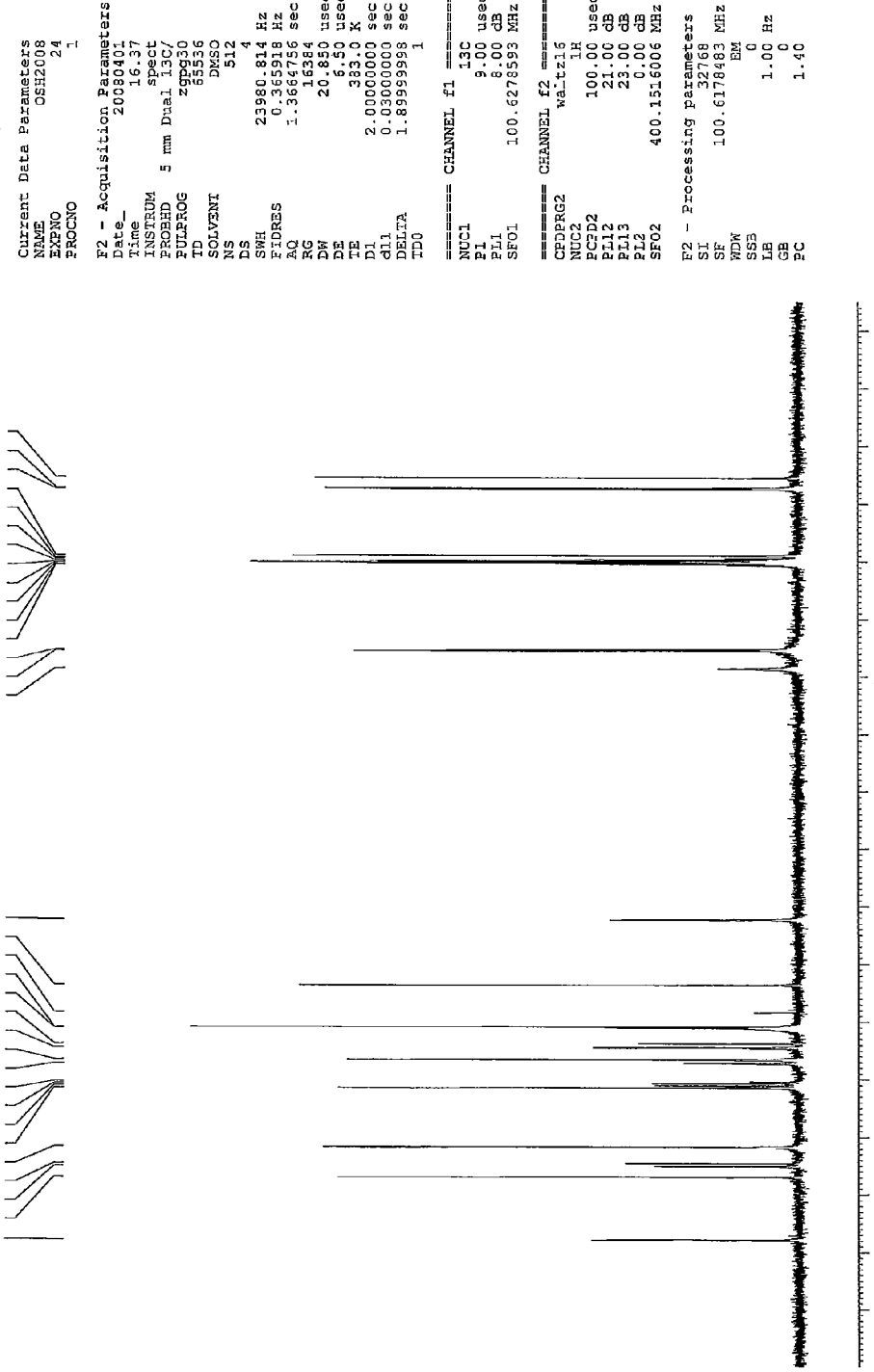
FIG. 3 shows $^{13}$C-NMR spectrum of the Q-BTBSA catalyst synthesized by using the present method described in Example 1.
Figure 4:
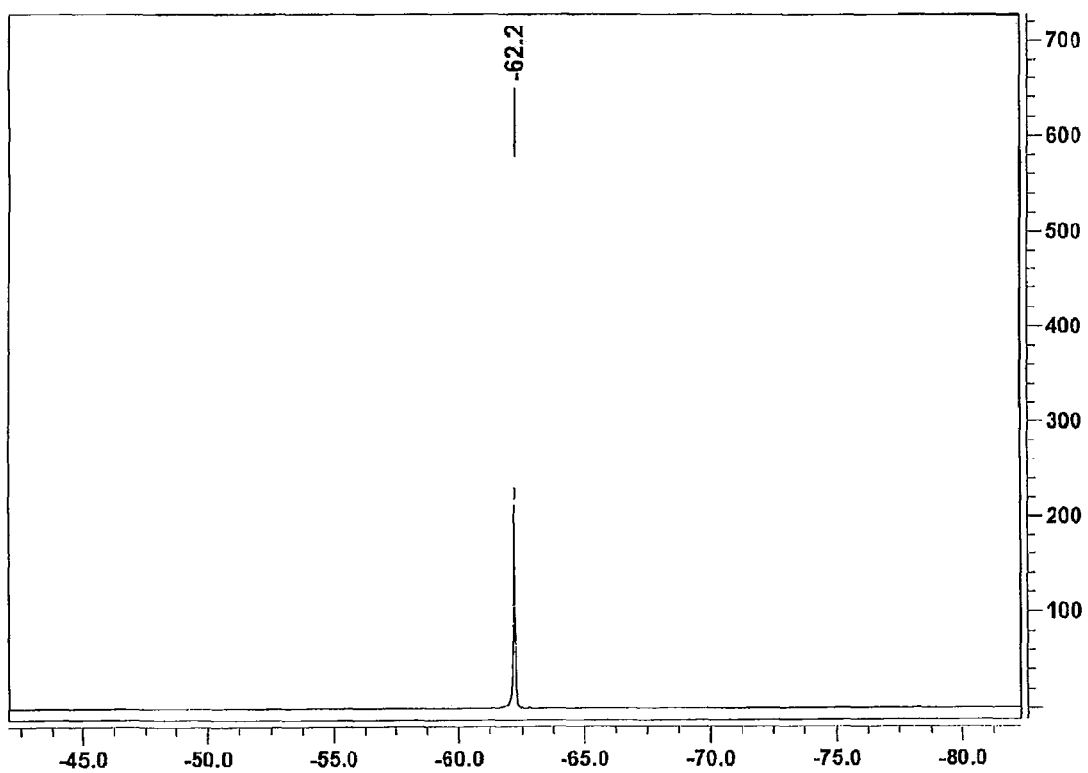
FIG. 4 shows $^{19}$F-NMR spectrum of the Q-BTBSA catalyst synthesized by using the present method described in Example 1.

The present invention relates to a compound of Formula 1 and its salt below:

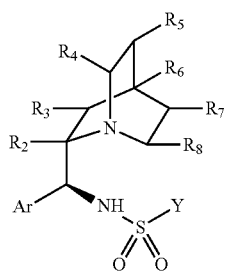

[Formula 1]

wherein,

Ar represents an aryl having 4 to 11 member ring, $R_2$, $R_3$, $R_4$, $R_6$, $R_7$ and $R_8$ represent hydrogen, $R_5$ represent an alkyl having 1 to 12 carbons, an alkenyl having 2 to 12 carbons, an alkynyl having 2 to 12 carbons, an alkoxy having 1 to 12 carbons or an aryl having 4 to 11 member ring, and Y represents an alkyl having 1 to 12 carbons, an alkenyl having 2 to 12 carbons, a cycloalkyl having 3 to 10 carbons, or an aryl having 4 to 11 member ring, with the proviso that Y is not para-toluene.

The present invention also relates to a compound of Formula 2 and its salt below:

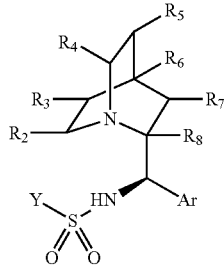

[Formula 2]

wherein,

Ar represents an aryl having 4 to 11 member ring, $R_2$, $R_4$, $R_5$, $R_6$, $R_7$ and $R_8$ represent hydrogen, $R_3$ represent an alkyl having 1 to 12 carbons, an alkenyl having 2 to 12 carbons, an alkynyl having 2 to 12 carbons, an alkoxy having 1 to 12 carbons or an aryl having 4 to 11 member ring, and Y represents an alkyl having 1 to 12 carbons, an alkenyl having 2 to 12 carbons, a cycloalkyl having 3 to 10 carbons, or an aryl having 4 to 11 member ring, with the proviso that Y is not para-toluene.

Preferably, said compound of Formula 1 or Formula 2 is a compound of Formula 1a or Formula 2a below.

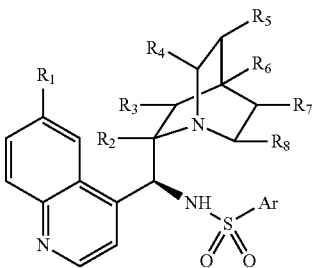

[Formula 1a]

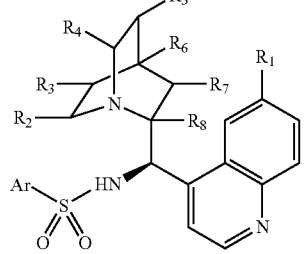

[Formula 2a]

wherein,

Ar represents an aryl group having 4 to 11 member ring, with the proviso that Ar is not para-toluene, and $R_1$ represents hydrogen, an alkyl having 1 to 12 carbons, an alkenyl having 2 to 12 carbons, an alkynyl having 2 to 12 carbons, an alkoxy having 1 to 12 carbons, or an aryl having 6 to 11 member ring, $R_2$, $R_4$, $R_6$, $R_7$ and $R_8$ represent hydrogen, and One of $R_3$ and $R_5$ represent an alkyl having 1 to 12 carbons, an alkenyl having 2 to 12 carbons, an alkynyl having 2 to 12 carbons, an alkoxy having 1 to 12 carbons or an aryl having 4 to 11 member ring and the other one is hydrogen.

Preferably, Ar may represent an aryl, having 6 to 10 member ring, unsubstituted or substituted with one or more substituents selected from the group consisting of halogen, amino, an aryl having 6 to 10 member ring, an alkyl having 1 to 6 carbons unsubstituted or substituted with halogen, an alkenyl having 2 to 6 carbons unsubstituted or substituted with halogen, and an alkoxy having 1 to 6 carbons unsubstituted or substituted with halogen, and One of $R_3$ and $R_5$ represent an alkyl having 1 to 6 carbons, an alkenyl having 2 to 6 carbons, an alkynyl having 2 to 6 carbons, or an alkoxy having 1 to 6 carbons and the other one is hydrogen.

More preferably, Ar may represent a phenyl group or a naphthyl group unsubstituted or substituted with one or more substituents selected from the group consisting of halogen, an alkyl having 1 to 4 carbons unsubstituted or substituted with halogen, an alkenyl having 2 to 4 carbons unsubstituted or substituted with halogen, and an alkoxy having 1 to 4 carbons unsubstituted or substituted with halogen.

In addition, said $R_1$ is, preferably, hydrogen or an alkoxy having 1 to 4 carbons.

Furthermore, in said compound of Formula 1a, $R_2$ may represent hydrogen, and $R_5$ may represent an alkyl having 1 to 4 carbons or an alkenyl having 2 to 4 carbons.

In said compound of Formula 2a, $R_8$ may represent hydrogen, $R_3$ may represent an alkyl having 1 to 4 carbons or an alkenyl having 2 to 4 carbons.

In addition, said compound of Formula 1 or Formula 2 is, preferably, a compound of Formula 1b or Formula 2b below.

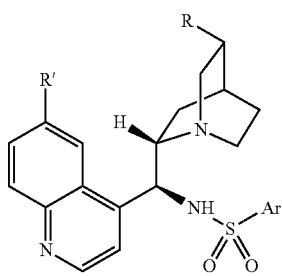

[Formula 1b]

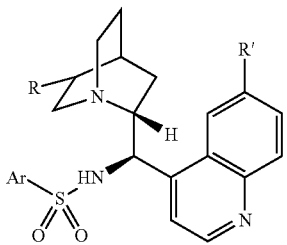

[Formula 2b]

wherein,

R represents ethyl or —CH=CH$_2$;

R' represents H or —OCH$_3$; and

Ar represents an aryl group having 4 to 11 member ring, with the proviso that Ar is not para-toluene.

In the above Formulas 1b and 2b, Ar may be selected from the group consisting of 3,5-bis(trifluoromethyl)benzene, ortho-toluene, meta-toluene, para-vinylbenzene, 1-naphthalene, 2-naphthalene, dimethylbenzene and phenyl.

The term "alkyl" used herein refers to radicals of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, unless described otherwise herein, a straight chain or branched chain alkyl has 30 or less carbon atoms (e.g., $C_1$-$C_{30}$ for straight chain, $C_3$-$C_{30}$ for branched chain), and more preferably 20 or less carbon atoms, in its backbone. Likewise, preferred cycloalkyl has 3 to 10 carbon atoms, and more preferably, 5, 6 or 7 carbons, in its ring structure.

Moreover, the term alkyl as used throughout the specification and claims is intended to include both "unsubstituted alkyl" and "substituted alkyl," the latter of which refers to alkyl moieties having substituents replacing hydrogen on one or more carbons of the hydrocarbon backbone. Such substituents can include, for example, halogen, hydroxyl, carbonyl, alkoxyl, and ester, phosphoryl, amine, amide, imine, thiol, thioether, thioester, sulfonyl, amino, nitro, or an organometallic moiety. It will be understood by those skilled in the art that the moieties substituted on the hydrocarbon chain themselves can be substituted, if appropriate. For example, the substituents of substituted alkyl may include amine, imine, amide, phosphoryl (including phosphonate and phosphine), sulfonyl (including sulfate and sulfonate) and a silyl group, having substituted and unsubstituted forms, as well as ether, thioether, selenoether, carbonyl (including ketone, aldehyde, carboxylate, and ester), —CF$_3$, —CN and the like. Exemplary substituted alkyl is described below. Cycloalkyl can be further substituted with alkyl, alkenyl, alkoxy, thioalkyl, aminoalkyl, carbonyl-substituted alkyl, CF$_3$, CN, and the like.

The terms "alkenyl" and "alkynyl" refer to unsaturated aliphatic groups, in view of length and possible substitution, similar to the above described alkyl, but contain at least one double or triple carbon-carbon bond, respectively.

As used herein, the term "amino" refers to —NH$_2$; the term "nitro" refers to —NO$_2$; the term "halogen" refers to —F, —Cl, —Br or —I; the term "thiol" refers to —SH; the term "hydroxyl" refers to —OH; the term "sulfonyl" refers to —SO$_2$—; and the term "organometallic" refers to a metallic atom (for example, mercury, zinc, lead, magnesium or lithium) or a metalloid (for example, silicon, arsenic or selenium) which is bonded directly to a carbon atom, such as a diphenylmethylsilyl group.

The term "alkoxy" as used herein refers to an alkyl group, as defined above, having an oxygen radical attached thereto. Representative alkoxyl groups include methoxy, ethoxy, propoxy, tert-butoxy and the like. "Ether" is two hydrocarbons covalently linked by oxygen. Accordingly, the substituent of alkyl, whereby alkyl is made to ether, is alkoxy, such as can be represented by one of —O-alkyl, —O— alkenyl, or —O-alkynyl, or analogues thereof.

The term "aryl" as used herein includes single ring and fused ring aromatic groups, having 4 to 11 member ring, more specifically, 6 to 10 member ring, which may include 0 to 4 heteroatoms, for example, benzene, naphthalene, pyrrole, furan, thiophene, imidazole, oxazole, thiazole, triazole, pyrazole, pyridine, pyrazine, pyridazine, quinoline and pyrimidine, and the like. The aromatic ring can be substituted at one or more ring positions with substituents as described above, for example, halogen, alkyl, alkenyl, alkynyl, hydroxyl, amino, nitro, thiol, amine, imine, amide, phosphonate, phosphine, carbonyl, carboxyl, silyl, ether, thioether, sulfonyl, selenoether, ketone, aldehyde, ester, or —CF$_3$, —CN, or the like.

The term "heteroatom" as used herein refers to an atom of any element other than carbon or hydrogen. Preferred heteroatoms are nitrogen, oxygen, sulfur, phosphorus and selenium.

As shown in the examples explained in detail, it has been found in the present invention that electronic nature or steric hindrance in substituents of aryl groups affects hardly the activity of catalysts and also optical selectivity. Those skilled in this technical field may recognize or identify that they can get similar results with compounds of Formula 1 or 2 having other substituents except for those mentioned above in most of specific aspects described herein without any further experiment. It is considered that these equivalents are included in the scope of the present invention.

The present invention also relates to a method for preparing a chiral hemiester comprising a step of reacting a prochiral compound or a meso-cyclic acid anhydride with a nucleophile in the presence of a compound of Formula I in a catalytic amount.

[Formula I]

wherein,

X represents an organic group containing 1-azabicyclo [2.2.2]octane moiety; and

Y represents alkyl, alkenyl, cycloalkyl, or aryl.

In the method of the present invention, the chiral hemiester may be prepared via a reaction of the following scheme 1.

[Scheme 1]

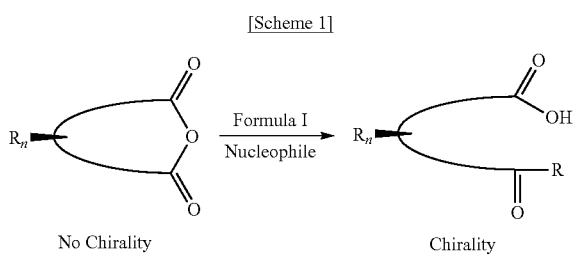

The term "nucleophile" as used herein is recognized in the art, and refers to a chemical moiety having a reactive pair of electrons. Examples of nucleophiles include uncharged compounds such as water, amines, mercaptans (thiols) and alcohols, and charged moieties such as alkoxides, thiolates, carbanions, and a variety of organic and inorganic anions.

The term "electrophile" is recognized in this field and refers to chemical moieties which can accept a pair of electrons from the nucleophiles as defined above. Electrophiles useful in the method of the present invention include cyclic compounds such as cyclic anhydrides.

The term "catalytic amount" is recognized in this field and refers to a substoichiometric amount, based on a reactant. As used herein, a catalytic amount refers to 0.0001 to 90 mole percent, more preferably 0.001 to 50 mole percent, still more preferably 0.01 to 10 mole percent, and even more preferably 0.1 to 5 mole percent, based on a reactant.

As discussed in more detail below, reactions contemplated in the present invention include reactions which are enantioselective, diastereoselective, and/or regioselective. An enantioselective reaction is a reaction which converts an achiral reactant to a chiral product enriched in one enantiomer. Enantioselectivity is generally quantified as "enantiomeric excess" (ee) defined as follows:

% Enantiomeric Excess $A(ee)$=(% Enantiomer $A$)−(% Enantiomer $B$)

where, A and B are the formed enantiomers.

Another term used together with enantioselectivity includes "optical purity" or "optical activity." An enantioselective reaction results in a product with an e. e. greater than zero. Preferred enantioselective reaction result in a product with an e. e. greater than 20%, more preferably greater than 50%, even more preferably greater than 70%, and most preferably greater than 80%.

Said nucleophile is used for the ring opening reaction of meso-cyclic acid anhydrides, and includes, preferably, alcohol, thiol or amine. Here, methanol, ethanol, 2-propen-1-ol, trifluoroethanol, benzyl alcohol, propanol or isopropanol may be used as an alcohol, and preferably, methanol may be used. Said alcohol may be used in an amount of 1 to 100 equivalents, preferably, 1 to 20 equivalents, and most preferably 1 to 10 equivalents relative to a meso-cyclic acid anhydride compound.

It is preferred that said pro chiral compound or meso-cyclic acid anhydride is a cyclic acid anhydride, a substituted succinic acid anhydride or a substituted glutaric acid anhydride.

Preferably, said nucleophile is used in an amount of 1 to 20 equivalents, based on a prochiral compound or meso-cyclic acid anhydride.

Preferably, said compound of Formula I is used in an amount of 0.1 to 30 mol %, based on a prochiral or meso-cyclic acid anhydride. More preferably, it may be used in an amount of 0.1 to 20 mol %, and most preferably 0.1 to 10 mol %.

Preferably, said reaction is performed in the presence of an aprotic solvent.

Said aprotic solvent includes ethylvinyl ether, dimethoxyethane, methyl t-butyl ether, diethyl ether, diisopropyl ether, tetrahydrofuran, and dioxane, and preferably diisopropyl ether, or methyl t-butyl ether, and the like may be used alone or in combination of 2 or more species thereof. More preferably, diisopropyl ether is used.

Furthermore, the reaction may be performed at a reaction temperature of −50 to 100° C., preferably −20 to 50° C., more preferably −20 to 30° C., and most preferably 5 to 25° C.

According to embodiments of the present invention, the derivatized compounds of Formula I were compared with and the stereoselective ring opening reactions of various prochiral or meso-cyclic acid anhydrides using methanol as a nucleophile were investigated. The concerned hemiesters were converted to the corresponding ester amides by reacting hemiesters with (R)-1-(1-naphthyl)ethyl amine according to the known method (H. Han, *Tetrahedron Lett.* 2004, 45, 3301-3304), and then analyzed by high performance liquid chromatography (HPLC) to determine the enantiomeric excess. In addition, it has been found that the concerned catalyst could be easily reused using acid-base extraction processes.

Since various chiral hemiesters prepared via the present invention include two carbonyl groups having different characteristics, they may be used in synthesizing stereochemically or pharmaceutically useful chiral compounds in accordance with the conventional processes.

The present invention also relates to a method for preparing said compound of Formula 1 or 2 comprising reacting an amine of Formula 3 or 4 below with a sulfonyl derivative of Formula 5 below:

[Formula 3]

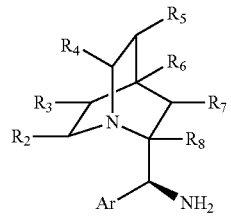

[Formula 4]

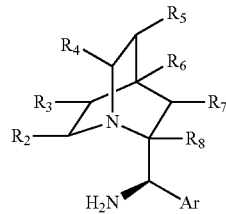

[Formula 5]

wherein,

Ar represents an aryl having 4 to 11 member ring, $R_2$, $R_4$, $R_6$, $R_7$ and $R_8$ represent hydrogen, One of $R_3$ and $R_5$ represent an alkyl having 1 to 12 carbons, an alkenyl having 2 to 12 carbons, an alkynyl having 2 to 12 carbons, an alkoxy having 1 to 12 carbons or an aryl having 4 to 11 member ring and the other one is hydrogen, Y represents an alkyl having 1 to 12 carbons, an alkenyl having 2 to 12 carbons, a cycloalkyl having 3 to 10 carbons, or an aryl having 4 to 11 member ring, with the proviso that Y is not para-toluene, and Z represents a halogen atom.

Preferably, said compound of Formula 3 is a compound of Formula 3a.

[Formula 3a]

R₁ represents hydrogen, an alkyl having 1 to 12 carbons, an alkenyl having 2 to 12 carbons, an alkynyl having 2 to 12 carbons, an alkoxy having 1 to 12 carbons, or an aryl having 4 to 11 member ring, R₂, R₃, R₄, R₆, R₇ and R₈ represent hydrogen, and R₅ represent an alkyl having 1 to 12 carbons, an alkenyl having 2 to 12 carbons, an alkynyl having 2 to 12 carbons, an alkoxy having 1 to 12 carbons or an aryl having 4 to 11 member ring.

Preferably, said compound of Formula 4 is a compound of Formula 4a.

[Formula 4a]

wherein,

R₁ represents hydrogen, an alkyl having 1 to 12 carbons, an alkenyl having 2 to 12 carbons, an alkynyl having 2 to 12 carbons, an alkoxy having 1 to 12 carbons, or an aryl having 4 to 11 member ring, R₂, R₄, R₅, R₆, R₇ and R₉ represent hydrogen, and R₃ represent an alkyl having 1 to 12 carbons, an alkenyl having 2 to 12 carbons, an alkynyl having 2 to 12 carbons, an alkoxy having 1 to 12 carbons or an aryl having 4 to 11 member ring.

Preferably, said Y may represent an aryl unsubstituted or substituted with one or more substituents selected from the group consisting of halogen, amino, an aryl having 4 to 11 member ring, an alkyl, having 1 to 6 carbons, unsubstituted or substituted with halogen, an alkenyl, having 2 to 6 carbons, unsubstituted or substituted with halogen, and an alkoxy, having 1 to 6 carbons, unsubstituted or substituted with halogen.

Preferably, benzene sulfonyl chloride or naphthalene sulfonyl chloride, unsubstituted or substituted, is used as said sulfonyl chloride derivative.

In the method of the present invention, said compound of Formula I may be prepared according to the following schemes.

[Scheme 2]

[Scheme 3]

wherein,

R is ethyl or —CH=CH₂; R' is H or —OCH₃ and Ar is an aryl group, with the proviso that Ar is not para-toluene.

Preferably, in said Scheme 2 or 3, Ar is unsubstituted or substituted benzene or naphthalene, with the proviso that Ar is not para-toluene.

More preferably, in said Scheme 2 or 3, Ar may be selected from the group consisting of 3,5-bis(trifluoromethyl)benzene, ortho-toluene, meta-toluene, para-vinylbenzene, 1-naphthalene, 2-naphthalene, dimethylbenzene and phenyl.

Mode for Invention

The preset invention is explained in more detail by the following examples. The examples below illustrate aspects of the present invention, but are not intended to restrict the scope of the present invention.

EXAMPLE

Method of Synthesizing Derivatized Bifunctional Cinchona Alkaloid Organocatalysts A derivatized bifunctional cinchona alkaloid catalyst was synthesized by a method comprising a step of reacting an amine prepared from a cinchona alkaloid via epimerization, with 1 equivalent of a sulfonyl chloride derivative in the presence of base. Said organocatalysts of Formula I may be synthesized from 9-amino(9-deoxy)epicinchona alkaloids described in a literature [*Organic Letters* 2005, 7, 1967]. For example, they were prepared by reacting dihydroquinine or quinine with diphenyl phosphoryl azide using triphenyl phosphine and diisopropyl azodicarboxylate to replace a hydroxyl group with amine, and then reacting the resulting product with a sulfonyl chloride derivative, followed by separating and purifying.

Example 1

Preparation of Q-BTBSA (Quinine-(Bis)-3,5-Trifluoromethyl Benzene Sulfonamide) Catalyst 3,5-Bis(trifluoromethyl)benzene sulfonyl chloride (3.42 g, 10.94 mmol) was added to a solution of amine (I) (3.54 g, 10.94 mmol) in anhydrous methylene chloride (50 mL) under argon at room temperature, and then triethyl amine (1.52 mL, 10.94 mmol) was added thereto. The mixed solution was stirred overnight at room temperature, distilled water (30 mL) was added thereto and stirred for 10 minutes to separate organic layer. The organic layer was dried with $Na_2SO_4$ and concentrated. The residue was purified by silica gel column chromatography (5% methanol in ethyl acetate) to obtain Q-BTBSA (5.9 g, 89.5%) as white solid.

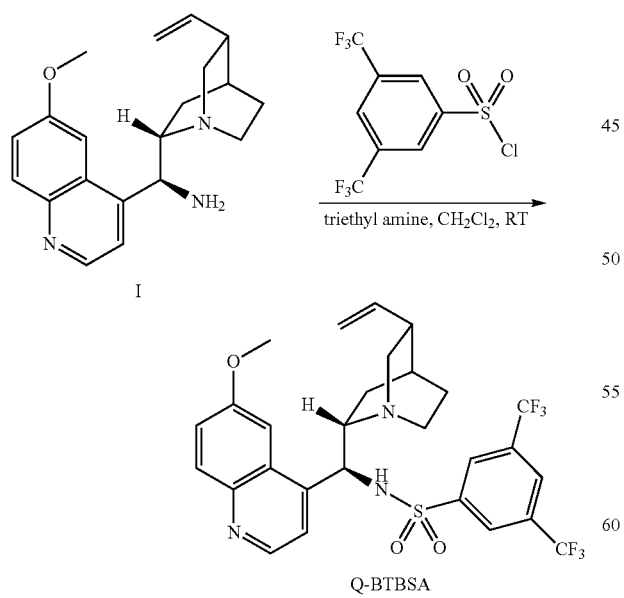

$^1$H NMR (300 MHz, d6-DMSO, 110° C.) δ 0.58-0.65 (m, 1H), 1.18-1.25 (m, 1H), 1.33-1.67 (m, 3H), 2.14-2.31 (m, 1H), 2.45-2.52 (m, 1H, overlapped with DMSO), 2.60-2.73 (m, 1H), 2.88-3.13 (m, 2H), 3.20-3.40 (m, 1H), 3.93 (s, 3H), 4.91 (t, J=1.5, 0.5H), 4.97 (td, 3J=17.1, 3J=1.5, 2J=1.5 Hz, 1.5H), 5.78 (ddd, 3J=17.1, 3J=10.5, 3J=6.9 Hz, 1H), 7.33-7.38 (m, 2H), 7.47 (d, J=2.4 Hz, 1H), 7.82 (d, J=9 Hz, 1H), 7.90-8.00 (m, 3H), 8.54 (d, 4 J=4.2 Hz, 1H) ppm;

$^{13}$C NMR (100 MHz, d6-DMSO, 110° C.) δ; 25.49, 27.26, 27.45, 38.97, 40.11, 55.27, 55.49, 58.59, 102.32, 113.61, 120.87, 122.41 (q, J(C—F)=271 Hz), 124.47, 126.52, 127.19, 130.84 (q, 2J(C—C—F)=34 Hz), 131.42, 141.67, 144.53, 145.02, 146.91, 157.83 ppm;

$^{19}$F NMR (376 MHz, d6-DMSO, 45° C.) δ-62.2 ppm

Example 2

Preparation of Q-Salt-BTBSA (Quinine-Salt-(Bis)-3,5-Trifluoromethyl Benzene Sulfonamide) Catalyst Q-BTBSA catalyst of Example 1 (1.00 g, 1.67 mmol) was added to 35% HCl (0.34 g, 3.34 mmol), and then water is evaporated. The residue was vacuum drying to obtain Q-Salt-BTBSA (1.12 g, 100%) as yellow solid

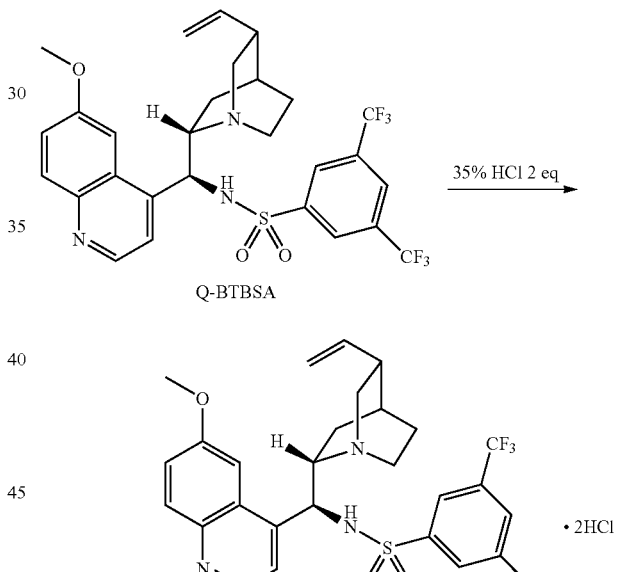

1H NMR (300 MHz, d6-D20, 80° C.) □ 01.49-1.58 (br, 1H), 2.32-2.39 (br, 1H), 2.56-2.57 (m, 3H), 3.41-3.46 (br, 1H), 3.92-4.06 (m, 2H), 4.34-4.47 (m, 3H, overlapped with D20), 5.68-5.88 (m, 2H), 6.25-6.42 (m, 1H), 7.83 (m, 1H), 8.16-8.19 (m, 1H), 8.32-8.51 (m, 5H), 9.33-9.37 (m, 1H)

Example 3

Preparation of QD-BTBSA (Quinidine-(Bis)-3,5-Trifluoromethyl Benzene Sulfonamide) Catalyst 3,5-Bis(trifluoromethyl)benzene sulfonyl chloride (1.83 g, 5.84 mmol) was added to a solution of amine (II) (1.89 g, 5.84 mmol) in anhydrous methylene chloride (50 mL) under argon at room temperature, and then triethyl amine (0.9 mL, 6.4 mmol) was added thereto. The mixed solution was stirred overnight at room temperature, distilled water (30 mL) was added thereto and stirred for 10 minutes to separate organic layer. The organic layer was dried with Na₂SO₄ and concentrated. The residue was purified by silica gel column chromatography (5% methanol in ethyl acetate) to obtain QD-BT-BSA (2.69 g, 76.8%) as white solid.

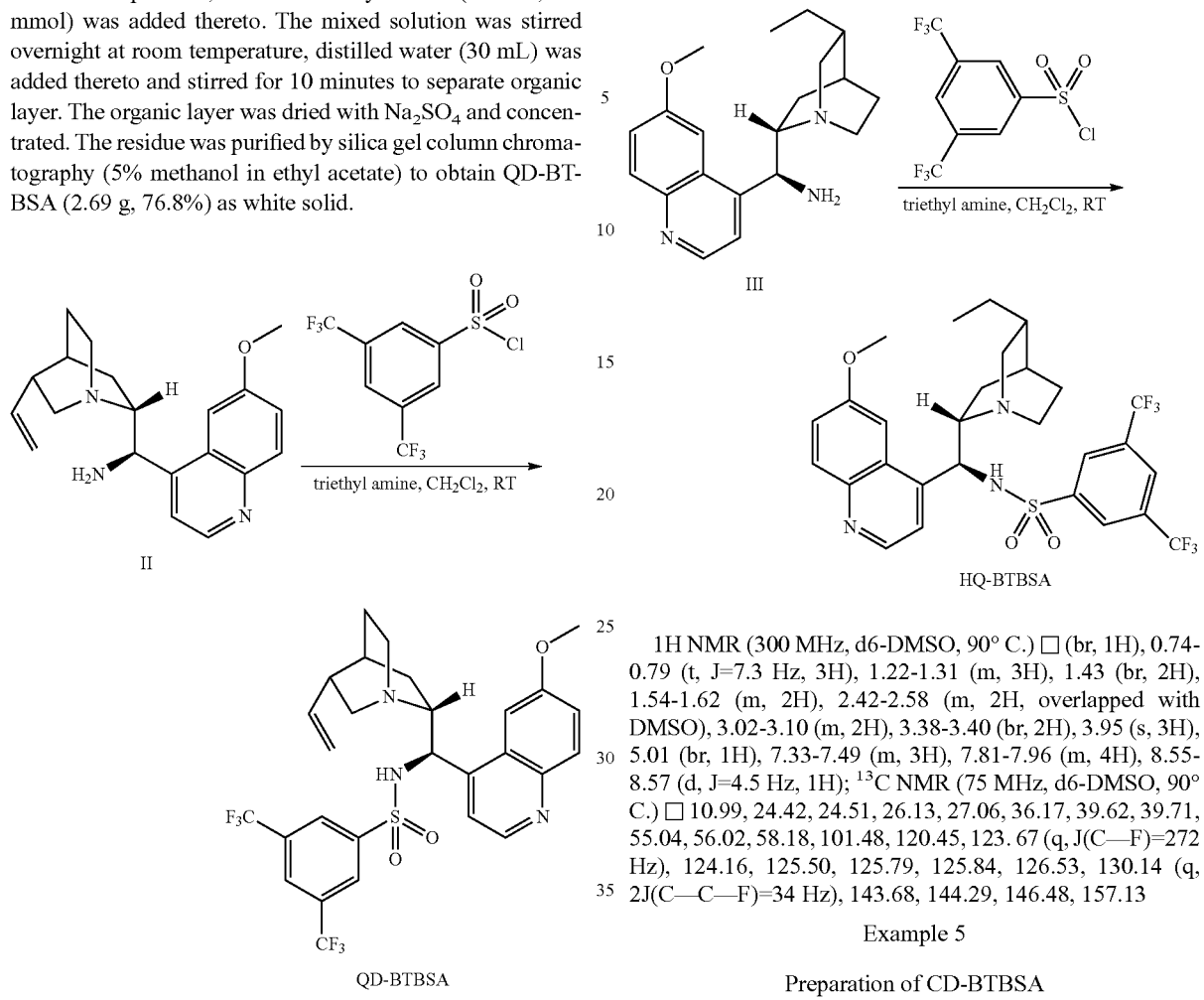

QD-BTBSA

1H NMR (300 MHz, d6-DMSO, 80° C.) 0.87-0.89 (m, 2H), 1.44-1.53 (m, 3H), 2.17-2.24 (m, 1H), 2.58-2.89 (m, 4H), 3.22-3.25 (m, 1H), 3.95 (s, 3H), 4.98-5.07 (m, 3H), 5.78-5.89 (m, 1H), 7.35-7.47 (m, 3H), 7.83-7.87 (d, J=9.1 Hz, 1H), 8.02-8.04 (m, 3H), 8.57-8.59 (d, J=4.5 Hz, 1H)

Example 4

Preparation of HQ-BTBSA
(Hydroquinine-(Bis)-3,5-Trifluoromethyl Benzene Sulfonamide) Catalyst 3,5-Bis(trifluoromethyl)benzene sulfonyl chloride (1.20 g, 3.84 mmol) was added to a solution of amine (III) (1.25 g, 3.84 mmol) in anhydrous methylene chloride (50 mL) under argon at room temperature, and then triethyl amine (0.54 mL, 3.84 mmol) was added thereto. The mixed solution was stirred at room temperature for 1 hour, distilled water (30 mL) was added thereto and stirred for 10 minutes to separate organic layer. The organic layer was dried with Na₂SO₄ and concentrated. The residue was purified by silica gel column chromatography (10% methanol in ethyl acetate) to obtain HQ-BTBSA (1.8 g, 77.9%) as white solid.

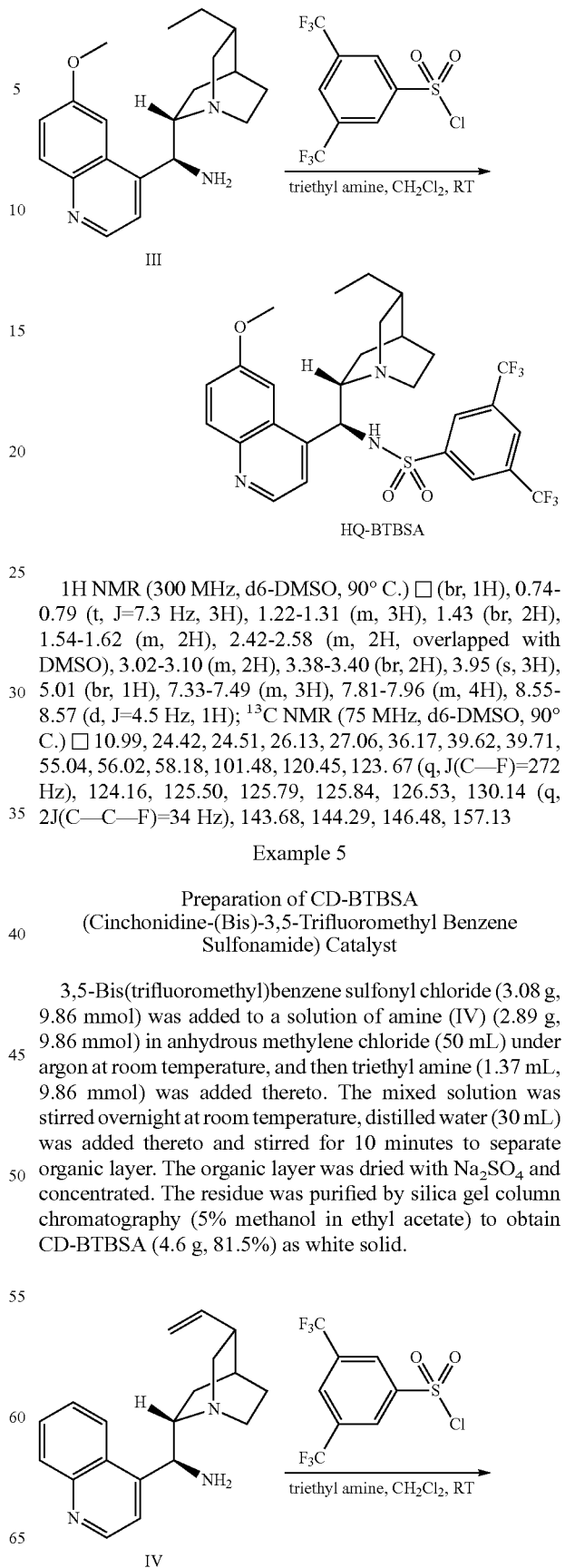

HQ-BTBSA

1H NMR (300 MHz, d6-DMSO, 90° C.) □ (br, 1H), 0.74-0.79 (t, J=7.3 Hz, 3H), 1.22-1.31 (m, 3H), 1.43 (br, 2H), 1.54-1.62 (m, 2H), 2.42-2.58 (m, 2H, overlapped with DMSO), 3.02-3.10 (m, 2H), 3.38-3.40 (br, 2H), 3.95 (s, 3H), 5.01 (br, 1H), 7.33-7.49 (m, 3H), 7.81-7.96 (m, 4H), 8.55-8.57 (d, J=4.5 Hz, 1H); ¹³C NMR (75 MHz, d6-DMSO, 90° C.) □ 10.99, 24.42, 24.51, 26.13, 27.06, 36.17, 39.62, 39.71, 55.04, 56.02, 58.18, 101.48, 120.45, 123. 67 (q, J(C—F)=272 Hz), 124.16, 125.50, 125.79, 125.84, 126.53, 130.14 (q, 2J(C—C—F)=34 Hz), 143.68, 144.29, 146.48, 157.13

Example 5

Preparation of CD-BTBSA
(Cinchonidine-(Bis)-3,5-Trifluoromethyl Benzene Sulfonamide) Catalyst 3,5-Bis(trifluoromethyl)benzene sulfonyl chloride (3.08 g, 9.86 mmol) was added to a solution of amine (IV) (2.89 g, 9.86 mmol) in anhydrous methylene chloride (50 mL) under argon at room temperature, and then triethyl amine (1.37 mL, 9.86 mmol) was added thereto. The mixed solution was stirred overnight at room temperature, distilled water (30 mL) was added thereto and stirred for 10 minutes to separate organic layer. The organic layer was dried with Na₂SO₄ and concentrated. The residue was purified by silica gel column chromatography (5% methanol in ethyl acetate) to obtain CD-BTBSA (4.6 g, 81.5%) as white solid.

-continued

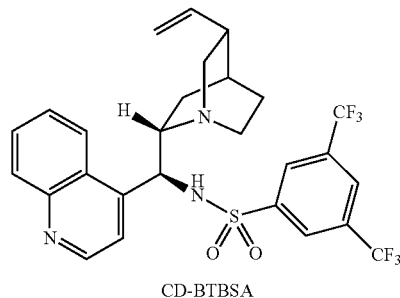

CD-BTBSA

¹H NMR (300 MHz, d₆-DMSO, 60° C.) δ 0.58 (br, 1H), 1.12 (br, 1H), 1.43-1.56 (m, 3H), 2.21 (br, 1H), 2.37-2.51 (m, 1H, overlapped with DMSO), 2.65-2.68 (m, 1H), 2.97-3.04 (m, 2H), 3.24 (br, 1H), 4.89-5.18 (m, 3H), 5.70-5.82 (m, 1H), 7.45-7.47 (d, J=4.5 Hz, 1H), 7.60-7.72 (m, 2H), 7.91-7.97 (m, 4H), 8.27-8.30 (d, J=8.4 Hz, 1H), 8.70-8.71 (d, J=4.5 Hz, 1H); ¹³C NMR (75 MHz, d₆-DMSO, 60° C.) δ 24.88, 26.67, 26.76, 38.50, 39.59, 51.89, 54.51, 59.01, 113.75, 119.26, 120.23 (q, J(C—F)=272 Hz), 122.69, 124.64, 126.12, 126.17, 126.50, 128.69, 129.40, 129.82 (q, ²J(C—C—F)=34 Hz), 141.43, 144.19, 147.53, 149.35

-continued

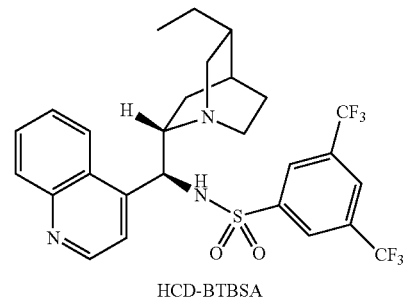

HCD-BTBSA

¹H NMR (300 MHz, d₆-DMSO, 90° C.) δ 0.59-0.65 (m, 1H), 0.73-0.78 (t, J=7.3 Hz, 3H), 1.10-1.29 (m, 3H), 1.39-1.41 (m, 2H), 1.52-1.63 (m, 2H), 2.42-2.54 (m, 2H, overlapped with DMSO), 3.01-3.09 (m, 2H), 3.30-3.33 (m, 1H), 5.11-5.13 (m, 1H), 7.47-7.49 (d, J=4.5 Hz, 1H), 7.56-7.71 (m, 2H), 7.91-7.96 (m, 3H), 8.27-8.30 (d, J=8.4 Hz, 1H), 8.70-8.72 (d, J=4.5 Hz, 1H); ¹³C NMR (75 MHz, d₆-DMSO, 90° C.) δ 11.01, 24.35, 24.38, 26.13, 27.04, 36.18, 39.58, 39.71, 55.97, 58.53, 122.51 (q, J(C—F)=273 Hz), 123.66, 124.24, 125.58, 126.00, 126.15, 127.28, 128.38, 129.23, 129.74 (q, ²J(C—C—F)=34 Hz), 143.26, 144.22, 147.46, 149.07

Example 6

Preparation of HCD-BTBSA (Hydrocinchonidine-(Bis)-3,5-Trifluoromethyl Benzene Sulfonamide) Catalyst 3,5-Bis(trifluoromethyl)benzene sulfonyl chloride (3.30 g, 10.56 mmol) was added to a solution of amine (V) (3.11 g, 10.56 mmol) in anhydrous methylene chloride (50 mL) under argon at room temperature, and then triethyl amine (1.47 mL, 10.56 mmol) was added thereto. The mixed solution was stirred overnight at room temperature, distilled water (30 mL) was added thereto and stirred for 10 minutes to separate organic layer. The organic layer was dried with Na₂SO₄ and concentrated. The residue was purified by silica gel column chromatography (5% methanol in ethyl acetate) to obtain HC-BTBSA (4.7 g, 78.2%) as white solid.

Example 7

Preparation of Q-PTSA (Quinine-Para-Toluene Sulfonamide) Catalyst

Para-toluene sulfonyl chloride (0.76 g, 3.99 mmol) was added to a solution of amine (I) (1.29 g, 3.99 mmol) in anhydrous methylene chloride (30 mL) under argon at room temperature, and then triethyl amine (0.61 mL, 4.39 mmol) was added thereto. The mixed solution was stirred overnight at room temperature, distilled water (20 mL) was added thereto and stirred for 10 minutes to separate organic layer. The organic layer was dried with Na₂SO₄ and concentrated. The residue was purified by silica gel column chromatography (10% methanol in ethyl acetate) to obtain Q-PTSA (1.0 g, 52.5%) as white solid.

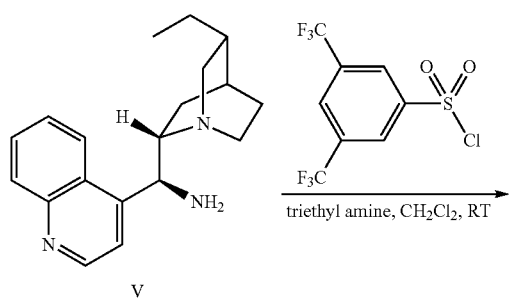

V

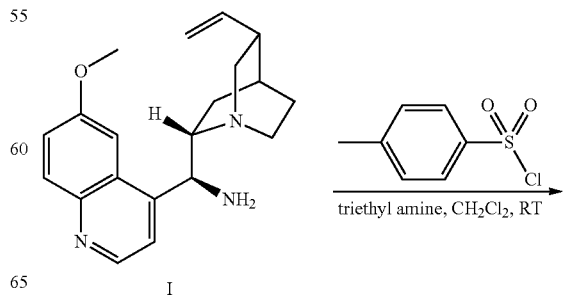

I

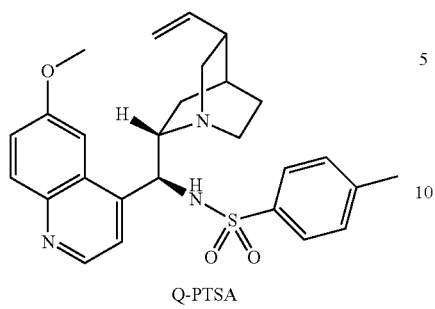

Q-PTSA

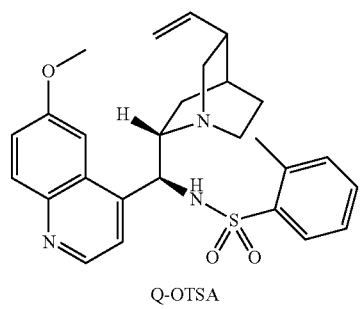

Q-OTSA $^1$H NMR (300 MHz, d$_6$-DMSO, 60° C.) δ 0.65-0.71 (br, 1H), 1.07-1.16 (br, 1H), 1.44-1.54 (m, 3H), 2.23 (s, 4H), 2.48-2.58 (m, 1H, overlapped with DMSO), 2.72-2.76 (m, 2H), 3.09-3.17 (dd, J=10.0 and 13.6 Hz, 2H), 3.94 (s, 3H), 4.88-4.99 (m, 3H), 5.68-5.79 (m, 1H), 6.98-7.01 (d, J=8.1 Hz, 2H), 7.33-7.42 (m, 5H), 7.86-7.89 (d, J=9.2 Hz, 1H), 8.58-8.59 (d, J=4.5 Hz, 1H); $^{13}$C NMR (75 MHz, d$_6$-DMSO, 60° C.) δ 20.39, 24.72, 26.70, 26.95, 38.52, 39.61, 51.68, 54.59, 55.21, 59.40, 101.05, 113.74, 119.84, 120.57, 126.04, 127.44, 128.23, 130.89, 137.17, 141.46, 141.77, 143.67, 146.85, 156.86

$^1$H NMR (300 MHz, d$_6$-DMSO, 70° C.) δ 0.57 (br, 1H), 1.04 (br, 1H), 1.37-1.46 (m, 3H), 2.16 (br, 1H), 2.42-2.50 (m, 5H, overlapped with DMSO), 2.61-2.76 (br, 2H), 3.03-3.11 (m, 1H), 3.92 (s, 3H), 4.85-4.97 (m, 3H), 5.68-5.73 (br, 1H), 6.95-7.00 (t, J=7.5 Hz, 1H), 7.10 (br, 1H), 7.21-7.25 (t, J=7.0 Hz, 1H), 7.35-7.38 (d, J=8.4 Hz, 2H), 7.54-7.56 (d, J=7.8 Hz, 2H), 7.84-7.87 (d, J=8.9 Hz, 1H), 8.58 (s, 1H); $^{13}$C NMR (75 MHz, d$_6$-DMSO, 70° C.) δ 19.21, 24.61, 26.60, 26.95, 38.47, 39.71, 51.56, 54.49, 55.11, 59.13, 101.15, 113.58, 119.60, 120.46, 124.74, 127.07, 128.15, 130.86, 131.36, 131.66, 136.37, 137.71, 141.40, 143.66, 146.74, 156.83

Example 8

Preparation of Q-OTSA (Quinine-Ortho-Toluene Sulfonamide) Catalyst

Ortho-toluene sulfonyl chloride (1.426 g, 7.48 mmol) was added to a solution of amine (I) (2.42 g, 7.48 mmol) in anhydrous methylene chloride (50 mL) under argon at room temperature, and then triethyl amine (1.14 mL, 8.23 mmol) was added thereto. The mixed solution was stirred overnight at room temperature, distilled water (30 mL) was added thereto and stirred for 10 minutes to separate organic layer. The organic layer was dried with Na$_2$SO$_4$ and concentrated. The residue was purified by silica gel column chromatography (5% methanol in ethyl acetate) to obtain Q-OTSA (2.86 g, 80%) as white solid.

Example 9

Preparation of Q-MTSA (Quinine-Meta-Toluene Sulfonamide) Catalyst

Meta-toluene sulfonyl chloride (1.44 g, 7.54 mmol) was added to a solution of amine (I) (2.44 g, 7.54 mmol) in anhydrous methylene chloride (50 ml) under argon at room temperature, and then triethyl amine (1.15 mL, 8.29 mmol) was added thereto. The mixed solution was stirred overnight at room temperature, distilled water (30 mL) was added thereto and stirred for 10 minutes to separate organic layer. The organic layer was dried with Na$_2$SO$_4$ and concentrated. The residue was purified by silica gel column chromatography (5% methanol in ethyl acetate) to obtain Q-MTSA (2.85 g, 79.1%) as white solid.

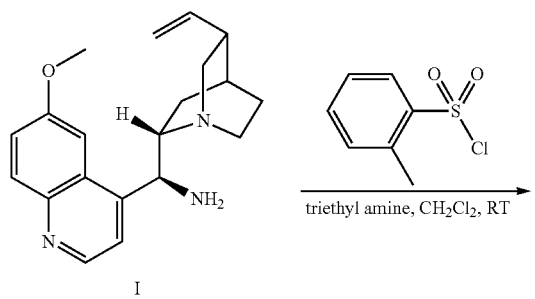

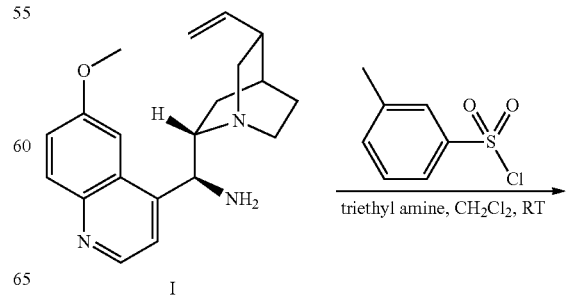

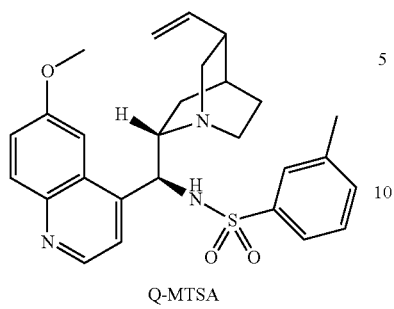

Q-MTSA

¹H NMR (300 MHz, d₆-DMSO, 60° C.) δ 0.67 (br, 1H), 1.11-1.15 (br, 1H), 1.46-1.51 (m, 3H), 2.07 (s, 3H), 2.21 (br, 1H), 2.49-2.59 (m, 1H, overlapped with DMSO), 2.71-2.80 (m, 2H), 3.09-3.17 (m, 2H), 3.94 (s, 3H), 4.87-4.98 (m, 3H), 5.67-5.78 (m, 1H), 7.06-7.17 (m, 3H), 7.28-7.30 (m, 1H), 7.36-7.46 (m, 3H), 7.86-7.89 (d, J=9.1 Hz, 1H), 8.56-8.57 (m, 1H); ¹³C NMR (75 MHz, d₆-DMSO, 60° C.) δ 20.05, 24.76, 26.74, 27.01, 38.55, 39.59, 51.82, 54.65, 55.19, 59.36, 101.12, 102.56, 113.67, 119.75, 120.55, 123.12, 126.32, 127.62, 130.91, 131.96, 137.48, 140.05, 141.46, 143.65, 146.84, 156.97

Example 10

Preparation of Q-1-NSA (Quinine-1-Naphthalene Sulfonamide) Catalyst

1-Naphthalene sulfonyl chloride (0.91 g, 4.0 mmol) was added to a solution of amine (I) (1.3 g, 4.0 mmol) in anhydrous methylene chloride (30 mL) under argon at room temperature, and then triethyl amine (0.67 mL, 4.8 mmol) was added thereto. The mixed solution was stirred at room temperature for 4 hours, distilled water (30 mL) was added thereto and stirred for 10 minutes to separate organic layer. The organic layer was dried with Na₂SO₄ and concentrated. The residue was purified by silica gel column chromatography (5% methanol in ethyl acetate) to obtain Q-1-NSA (1.6 g, 77.5%) as white solid.

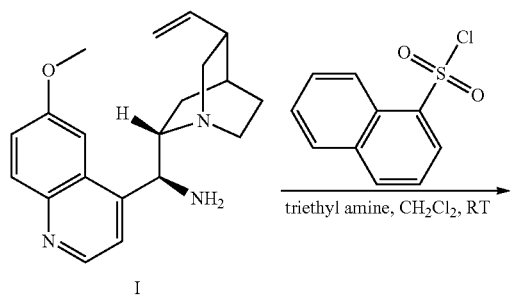

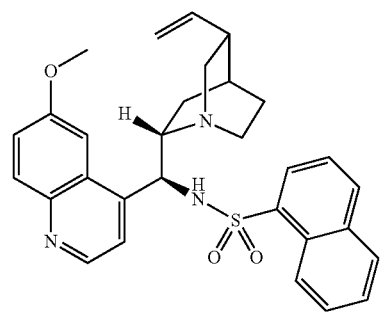

Q-1-NSA

¹H NMR (300 MHz, d₆-DMSO, 90° C.) δ 0.59-0.65 (m, 1H), 1.02-1.09 (m, 1H), 1.38-1.48 (m, 3H), 2.17 (br, 1H), 2.26-2.35 (m, 1H), 2.63-2.73 (m, 2H), 2.99-3.07 (m, 1H), 3.16 (br, 1H), 3.87 (s, 3H), 4.79-4.95 (m, 3H), 5.63-5.75 (m, 1H), 7.10-7.16 (t, J=7.8 Hz, 1H), 7.22-7.33 (m, 3H), 7.51-7.61 (m, 2H), 7.77-7.85 (m, 4H), 8.32 (s, 1H), 8.60-8.63 (d, J=8.4 Hz, 1H); ¹³C NMR (75 MHz, d₆-DMSO, 90° C.) δ 24.49, 26.50, 26.79, 38.31, 39.28, 54.50, 54.91, 58.45, 101.59, 113.38, 120.09, 122.79, 124.18, 125.75, 126.71, 127.01, 127.88, 128.01, 130.52, 132.78, 132.84, 134.61, 141.21, 143.43, 146.15, 156.51

Example 11

Preparation of Q-2-NSA (Quinine-2-Naphthalene Sulfonamide) Catalyst

2-Naphthalene sulfonyl chloride (1.32 g, 8.81 mmol) was added to a solution of amine (I) (1.88 g, 5.81 mmol) in anhydrous methylene chloride (50 under argon at room temperature, and then triethyl amine (0.97 mL, 6.98 mmol) was added thereto. The mixed solution was stirred overnight at room temperature, distilled water (40 mL) was added thereto and stirred for 10 minutes to separate organic layer. The organic layer was dried with Na₂SO₄ and concentrated. The residue was purified by silica gel column chromatography (5% methanol in ethyl acetate) to obtain Q-2-NSA (2.35 g, 79%) as white solid.

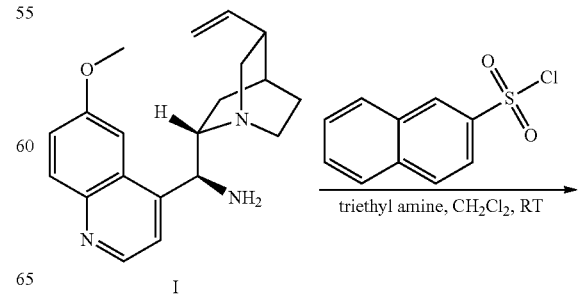

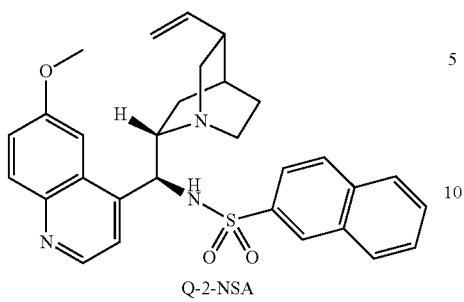

Q-2-NSA $^1$H NMR (300 MHz, d$_6$-DMSO, 50° C.) δ 0.61 (br, 1H), 1.08 (br, 1H), 1.39-1.47 (m, 3H), 2.17 (br, 1H), 2.45-2.50 (m, 1H, overlapped with DMSO), 2.73 (m, 2H), 3.03-3.11 (m, 2H), 3.91 (s, 3H), 4.86-4.97 (m, 3H), 5.69-5.74 (br, 1H), 7.26 (br, 1H), 7.43-7.44 (m, 2H), 7.51-7.61 (m, 3H), 7.69-7.76 (m, 3H), 7.83-7.86 (d, J=7.8 Hz, 1H), 8.02 (s, 1H), 8.51-8.52 (d, J=4.0 Hz, 1H); $^{13}$C NMR (75 MHz, d$_6$-DMSO, 50° C.) δ 24.82, 26.75, 26.98, 38.59, 39.71, 51.81, 54.66, 55.19, 59.34, 100.98, 102.77, 113.77, 119.71, 120.50, 121.85, 124.06, 126.77, 126.88, 127.18, 127.94, 128.01, 128.45, 130.76, 130.82, 133.48, 137.30, 141.54, 143.47, 146.90, 157.04

Example 12

Preparation of Q-BSA (Quinine-Benzene Sulfonamide) Catalyst

Benzene sulfonyl chloride (2.03 g, 11.51 mmol) was added to a solution of amine (I) (2.48 g, 7.67 mmol) in anhydrous methylene chloride (50 mL) under argon at room temperature, and then triethyl amine (0.97 mL, 9.20 mmol) was added thereto. The mixed solution was stirred overnight at room temperature, distilled water (40 mL) was added thereto and stirred for 10 minutes to separate organic layer. The organic layer was dried with Na$_2$SO$_4$ and concentrated. The residue was purified by silica gel column chromatography (5% methanol in ethyl acetate) to obtain Q-BSA (2.88 g, 81%) as white solid.

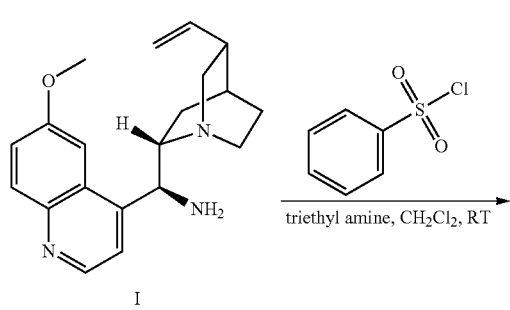

Q-BSA $^1$H NMR (300 MHz, d$_6$-DMSO, 50° C.) δ 0.61 (br, 1H), 1.09 (br, 1H), 1.42-1.49 (m, 3H), 2.19 (br, 1H), 2.47 (br, 1H, overlapped with DMSO), 2.74 (br, 2H), 3.04-3.12 (dd, J=10.0 and 13.5 Hz, 2H), 3.94 (s, 3H), 4.87-4.98 (m, 3H), 5.71 (br, 1H), 7.20-7.25 (m, 2H), 7.34-7.42 (m, 3H), 7.48-7.50 (m, 2H), 7.86-7.89 (d, J=9.1 Hz, 1H), 8.57-8.58 (d, J=4.5 Hz, 1H); $^{13}$C NMR (75 MHz, d$_6$-DMSO, 50° C.) δ 24.79, 26.76, 27.00, 38.59, 39.71, 51.81, 54.60, 55.25, 59.39, 101.00, 103.15, 113.77, 119.82, 120.74, 123.94, 126.02, 127.90, 131.02, 131.56, 140.27, 141.49, 143.61, 146.99, 157.08

Example 13

Preparation of Q-4-VBSA (Quinine-4-Vinyl Benzene Sulfonamide) Catalyst

4-Vinyl benzene sulfonyl chloride (1.97 g, 9.74 mmol) was added to a solution of amine (I) (2.10 g, 6.49 mmol) in anhydrous methylene chloride (50 mL) under argon at room temperature, and then triethyl amine (0.82 mL, 7.79 mmol) was added thereto. The mixed solution was stirred overnight at room temperature, distilled water (40 mL) was added thereto and stirred for 10 minutes to separate organic layer. The organic layer was dried with Na$_2$SO$_4$ and concentrated. The residue was purified by silica gel column chromatography (5% methanol in ethyl acetate) to obtain Q-4-VBSA (2.73 g, 86%) as white solid.

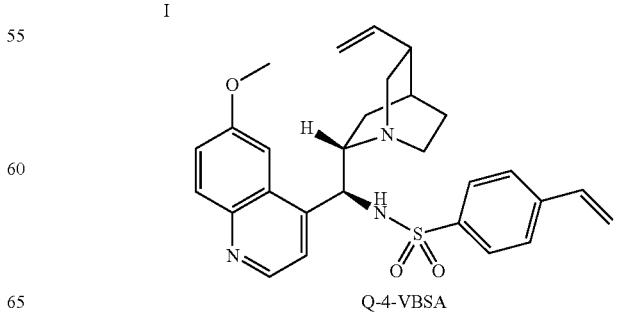

Q-4-VBSA $^1$H NMR (300 MHz, d$_6$-DMSO, 50° C.) δ 0.63-0.64 (br, 1H), 1.08-1.10 (br, 1H), 1.43-1.51 (m, 3H), 2.20 (br, 1H), 2.44-2.54 (br, 1H, overlapped with DMSO), 2.73 (br, 2H), 3.05-3.13 (dd, J=10.0 and 13.5 Hz, 2H), 3.94 (s, 3H), 4.88-4.99 (m, 3H), 5.34-5.38 (d, J=11.2 Hz, 1H), 5.68-5.86 (br, 2H), 6.61-6.71 (dd, J=10.9 and 17.6 Hz, 1H), 7.26-7.29 (m, 2H), 7.40-7.43 (m, 4H), 7.83-7.86 (d, J=9.1 Hz, 1H), 8.57-8.58 (d, J=4.5 Hz, 1H)

Example 14

Preparation of Q-MXSA (Quinine-Meta-Xylyl Sulfonamide) Catalyst

Meta-xylyl sulfonyl chloride (1.65 g, 5.59 mmol) was added to a solution of amine (I) (1.81 g, 5.59 mmol) in anhydrous methylene chloride (50 mL) under argon at room temperature, and then triethyl amine (0.78 mL, 5.59 mmol) was added thereto. The mixed solution was stirred overnight at room temperature, distilled water (40 mL) was added thereto and stirred for 10 minutes to separate organic layer. The organic layer was dried with Na$_2$SO$_4$ and concentrated. The residue was purified by silica gel column chromatography (5% methanol in ethyl acetate) to obtain Q-MXSA (2.17 g, 79%) as white solid.

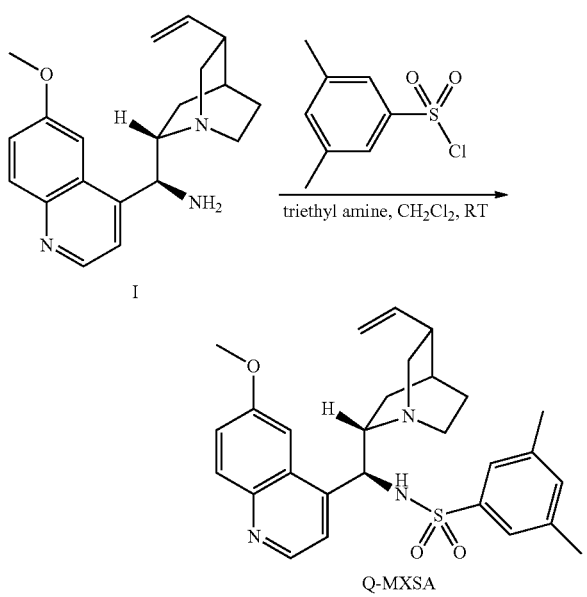

$^1$H NMR (300 MHz, d$_6$-DMSO, 70° C.) δ 0.67 (br, 1H), 1.11 (br, 1H), 1.48-1.51 (m, 3H), 2.03 (s, 6H), 2.22-2.24 (br, 1H), 2.50-2.64 (m, 11-1, overlapped with DMSO), 2.72-2.75 (m, 1H), 2.89 (br, 1H), 3.11-3.19 (m, 2H), 3.93 (s, 3H), 4.89-4.98 (m, 3H), 5.67-5.78 (m, 1H), 6.87 (s, 1H), 6.96 (s, 1H), 7.39 (s, 3H), 7.85-7.89 (d, J=8.9 Hz, 1H), 8.55-8.57 (d, J=4.5 Hz, 1H); $^{13}$C NMR (75 MHz, d$_6$-DMSO, 70° C.) δ 19.88, 24.73, 26.71, 26.96, 38.48, 39.55, 51.69, 54.66, 55.11, 59.28, 101.50, 113.59, 119.93, 120.36, 123.57, 124.39, 127.48, 130.79, 132.52, 137.19, 139.83, 141.37, 143.71, 146.62, 156.86

Desymmetrization of Prochiral or Meso-Cyclic Acid Anhydrides by Catalysts

Example 15

0.5 mmol of an anhydride (1a) was dissolved in 5 mL of diethyl ether at 20° C., 10 mol % of an organocatalyst (Q-BT-BSA) was added thereto, 10 equivalents of methanol was added once thereto, and the mixture was stirred at normal temperature for 1 hour. This reaction was quenched using an aqueous solution of dilute hydrochloric acid (1N, 3 mL). The aqueous layer was extracted with ethyl acetate (2×10 mL), and the combined organic layer was dried with MgSO$_4$ and concentrated. The residue was purified by flash chromatography (25% ethyl acetate in normal-hexane) to obtain a hemiester (2a, 91% yield). According to the already known method of the following Scheme 4 (H. Han, *Tetrahedron Lett.* 2004, 45, 3301-3304), it was determined to obtain an enantiomeric excess of 96% by reacting the hemiester and R-1-(1-naphthyl)ethyl amine to be converted to an ester amide corresponding to the hemiester. The enantioselectivity was measured using high performance liquid chromatography (Hypersil, 40:1, hexane:isopropyl alcohol, 1 mL/min., t (side product)=8.50 min., t (main product)=11.79 min)

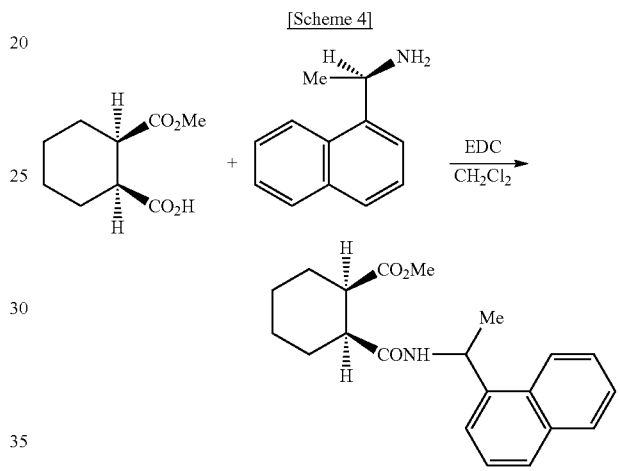

[Scheme 4]

$^1$H NMR (300 MHz, CDCl$_3$) δ 1.36-1.62 (m, 4H), 1.72-1.84 (m, 2H), 1.96-2.10 (m, 2H), 2.80-2.92 (m, 2H), 3.68 (s, 3H); $^{13}$C NMR (75 MHz, CDCl$_3$) δ 23.8, 23.9, 26.1, 26.4, 42, 5, 42.7, 51.9, 174.2, 180.3

Example 16

0.5 mmol of an anhydride (1a) was dissolved in 5 mL of diethyl ether at 20° C., 5 mol % of an organocatalyst (Q-BT-BSA) was added thereto, 10 equivalents of methanol was added once thereto, and the mixture was stirred at normal temperature for 2 hours. This reaction was quenched using an aqueous solution of dilute hydrochloric acid (1N, 3 mL). The aqueous layer was extracted with ethyl acetate (2×10 mL), and the combined organic layer was dried with MgSO$_4$ and concentrated. The residue was purified by flash chromatography (25% ethyl acetate in normal-hexane) to obtain a hemiester (2a, 92% yield). According to the already known method of the above Scheme 4 (H. Han, *Tetrahedron Lett.* 2004, 45, 3301-3304), it was determined to obtain an enantiomeric excess of 95% by reacting the hemiester and R-1-(1-naphthyl)ethyl amine to be converted to an ester amide corresponding to the hemiester. The enantioselectivity was measured using high performance liquid chromatography (Hypersil, 40:1, hexane:isopropyl alcohol, 1 mL/min., t (side product)=8.50 min., t (main product)=11.79 min).

Example 17

0.5 mmol of an anhydride (1a) was dissolved in 5 mL of diethyl ether at 20° C., 1 mol % of an organocatalyst (Q-BT- BSA) was added thereto, 10 equivalents of methanol was added once thereto, and the mixture was stirred at normal temperature for 6 hours. This reaction was quenched using an aqueous solution of dilute hydrochloric acid (1N, 3 mL). The aqueous layer was extracted with ethyl acetate (2×10 mL), and the combined organic layer was dried with MgSO$_4$ and concentrated. The residue was purified by flash chromatography (25% ethyl acetate in normal-hexane) to obtain a hemiester (2a, 92% yield). According to the already known method of the above Scheme 4 (H Han, *Tetrahedron Lett.* 2004, 45, 3301-3304), it was determined to obtain an enantiomeric excess of 95% by reacting the hemiester and R-1-(1-naphthyl)ethyl amine to be converted to an ester amide corresponding to the hemiester. The enantioselectivity was measured using high performance liquid chromatography (Hypersil, 40:1, hexane:isopropyl alcohol, 1 mL/min., t (side product)=8.50 min., t (main product)=11.79 min).

Example 18

0.5 mmol of an anhydride (1a) was dissolved in 5 mL of diethyl ether at 20° C., 0.5 mol % of an organocatalyst (Q-BT-BSA) was added thereto, 10 equivalents of methanol was added once thereto, and the mixture was stirred at normal temperature for 20 hours. This reaction was quenched using an aqueous solution of dilute hydrochloric acid (1N, 3 mL). The aqueous layer was extracted with ethyl acetate (2×10 mL), and the combined organic layer was dried with MgSO$_4$ and concentrated. The residue was purified by flash chromatography (25% ethyl acetate in normal-hexane) to obtain a hemiester (2a, 89% yield). According to the already known method of the above Scheme 4 (H. Han, *Tetrahedron Lett.* 2004, 45, 3301-3304), it was determined to obtain an enantiomeric excess of 93% by reacting the hemiester and R-1-(1-naphthyl)ethyl amine to be converted to an ester amide corresponding to the hemiester. The enantioselectivity was measured using high performance liquid chromatography (Hypersil, 40:1, hexane:isopropyl alcohol, 1 mL/min., t (side product)=8.50 min., t (main product)=11.79 min.).

Example 19

0.5 mmol of an anhydride (1a) was dissolved in 5 mL of diethyl ether at 20° C., 10 mol % of an organocatalyst (Q-PTSA) was added thereto, 10 equivalents of methanol was added once thereto, and the mixture was stirred at normal temperature for 1 hour. This reaction was quenched using an aqueous solution of dilute hydrochloric acid (1N, 3 mL). The aqueous layer was extracted with ethyl acetate (2×10 mL), and the combined organic layer was dried with MgSO$_4$ and concentrated. The residue was purified by flash chromatography (25% ethyl acetate in normal-hexane) to obtain a hemiester (2a, 95% yield). According to the already known method of the above Scheme 4 (H. Han, *Tetrahedron Lett.* 2004, 45, 3301-3304), it was determined to obtain an enantiomeric excess of 92% by reacting the hemiester and R-1-(1-naphthyl)ethyl amine to be converted to an ester amide corresponding to the hemiester. The enantioselectivity was measured using high performance liquid chromatography (Hypersil, 40:1, hexane:isopropyl alcohol, 1 mL/min., t (side product)=8.50 min., t (main product)=11.79 min).

Example 20

0.5 mmol of an anhydride (1a) was dissolved in 5 mL of diethyl ether at 20° C., 5 mol % of an organocatalyst (Q-1-NSA) was added thereto, 10 equivalents of methanol was added once thereto, and the mixture was stirred at normal temperature for 1 hour. This reaction was quenched using an aqueous solution of dilute hydrochloric acid (1N, 3 mL). The aqueous layer was extracted with ethyl acetate (2×10 mL), and the combined organic layer was dried with MgSO$_4$ and concentrated. The residue was purified by flash chromatography (25% ethyl acetate in normal-hexane) to obtain a hemiester (2a, 95% yield). According to the already known method of the above Scheme 4 (H. Han, *Tetrahedron Lett.* 2004, 45, 3301-3304), it was determined to obtain an enantiomeric excess of 92% by reacting the hemiester and R-1-(1-naphthyl)ethyl amine to be converted to an ester amide corresponding to the hemiester. The enantioselectivity was measured using high performance liquid chromatography (Hypersil, 40:1, hexane:isopropyl alcohol, 1 mL/min., t (side product)=8.50 min., t (main product)=11.79 min.).

Example 21

0.5 mmol of an anhydride (1a) was dissolved in 5 mL of diethyl ether at 20° C., 5 mol % of an organocatalyst (Q-2-NSA) was added thereto, 10 equivalents of methanol was added once thereto, and the mixture was stirred at normal temperature for 1 hour. This reaction was quenched using an aqueous solution of dilute hydrochloric acid (1N, 3 mL). The aqueous layer was extracted with ethyl acetate (2×10 mL), and the combined organic layer was dried with MgSO$_4$ and concentrated. The residue was purified by flash chromatography (25% ethyl acetate in normal-hexane) to obtain a hemiester (2a, 95% yield). According to the already known method of the above Scheme 4 (H. Han, *Tetrahedron Lett.* 2004, 45, 3301-3304), it was determined to obtain an enantiomeric excess of 92% by reacting the hemiester and R-1-(1-naphthyl)ethyl amine to be converted to an ester amide corresponding to the hemiester. The enantioselectivity was measured using high performance liquid chromatography (Hypersil, 40:1, hexane:isopropyl alcohol, 1 mL/min., t (side product)=8.50 min., t (main product)=11.79 min.).

Example 22

0.5 mmol of an anhydride (1a) was dissolved in 5 mL of diisopropyl ether at 20° C., 5 mol % of an organocatalyst (Q-BSA) was added thereto, 10 equivalents of methanol was added once thereto, and the mixture was stirred at normal temperature for 1.5 hours. This reaction was quenched using an aqueous solution of dilute hydrochloric acid (1N, 3 mL). The aqueous layer was extracted with ethyl acetate (2×10 mL), and the combined organic layer was dried with MgSO$_4$ and concentrated. The residue was purified by flash chromatography (25% ethyl acetate in normal-hexane) to obtain a hemiester (2a, 99% yield). According to the already known method of the above Scheme 4 (H. Han, *Tetrahedron Lett.* 2004, 45, 3301-3304), it was determined to obtain an enantiomeric excess of 96% by reacting the hemiester and R-1-(1-naphthyl)ethyl amine to be converted to an ester amide corresponding to the hemiester. The enantioselectivity was measured using high performance liquid chromatography (Hypersil, 40:1, hexane:isopropyl alcohol, 1 mL/min., t (side product)=8.50 min., t (main product)=11.79 min.).

Example 23

0.5 mmol of an anhydride (1a) was dissolved in 5 mL of methyl t-butyl ether at 20° C., 5 mol % of an organocatalyst (Q-4-VBSA) was added thereto, 10 equivalents of methanol was added once thereto, and the mixture was stirred at normal temperature for 1 hour. This reaction was quenched using an aqueous solution of dilute hydrochloric acid (1N, 3 mL). The aqueous layer was extracted with ethyl acetate (2×10 mL), and the combined organic layer was dried with MgSO₄ and concentrated. The residue was purified by flash chromatography (25% ethyl acetate in normal-hexane) to obtain a hemiester (2a, 99% yield). According to the already known method of the above Scheme 4 (H. Han, *Tetrahedron Lett.* 2004, 45, 3301-3304), it was determined to obtain an enantiomeric excess of 95% by reacting the hemiester and R-1-(1-naphthyl)ethyl amine to be converted to an ester amide corresponding to the hemiester. The enantioselectivity was measured using high performance liquid chromatography (Hypersil, 40:1, hexane:isopropyl alcohol, 1 mL/min., t (side product)=8.50 min., t (main product)=11.79 min).

Example 24

0.5 mmol of an anhydride (1a) was dissolved in 5 mL of diisopropyl ether at 20° C., 5 mol % of an organocatalyst (Q-4-VBSA) was added thereto, 10 equivalents of methanol was added once thereto, and the mixture was stirred at normal temperature for 1.5 hours. This reaction was quenched using an aqueous solution of dilute hydrochloric acid (1N, 3 The aqueous layer was extracted with ethyl acetate (2×10 mL), and the combined organic layer was dried with MgSO₄ and concentrated. The residue was purified by flash chromatography (25% ethyl acetate in normal-hexane) to obtain a hemiester (2a, 99% yield). According to the already known method of the above Scheme 4 (H. Han, *Tetrahedron Lett.* 2004, 45, 3301-3304), it was determined to obtain an enantiomeric excess of 95% by reacting the hemiester and R-1-(1-naphthyl)ethyl amine to be converted to an ester amide corresponding to the hemiester. The enantioselectivity was measured using high performance liquid chromatography (Hypersil, 40:1, hexane:isopropyl alcohol, 1 mL/min., t (side product)=8.50 min., t (main product)=11.79 min).

Example 25

0.5 mmol of an anhydride (1a) was dissolved in 10 mL, of diisopropyl ether at −20° C., 5 mol % of an organocatalyst (Q-4-VBSA) was added thereto, 10 equivalents of methanol was added once thereto, and the mixture was stirred at −20° C. for 4 hours. This reaction was quenched using an aqueous solution of dilute hydrochloric acid (1N, 3 mL). The aqueous layer was extracted with ethyl acetate (2×10 mL), and the combined organic layer was dried with MgSO₄ and concentrated. The residue was purified by flash chromatography (25% ethyl acetate in normal-hexane) to obtain a hemiester (2a, 99% yield). According to the already known method of the above Scheme 4 (H. Han, *Tetrahedron Lett.* 2004, 45, 3301-3304), it was determined to obtain an enantiomeric excess of 97% by reacting the hemiester and R-1-(1-naphthyl)ethyl amine to be converted to an ester amide corresponding to the hemiester. The enantioselectivity was measured using high performance liquid chromatography (Hypersil, 40:1, hexane:isopropyl alcohol, 1 mL/min., t (side product)=8.50 min., t (main product)=11.79 min.).

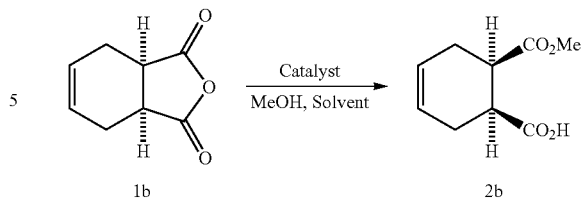

Example 26

0.5 mmol of an anhydride (1b) was dissolved in 5 mL of diethyl ether at 20° C., 5 mol % of an organo catalyst (Q-BTBSA) was added thereto, 10 equivalents of methanol was added once thereto, and the mixture was stirred at normal temperature for 1.5 hours. This reaction was quenched using an aqueous solution of dilute hydrochloric acid (1N, 3 mL). The aqueous layer was extracted with ethyl acetate (2×10 mL), and the combined organic layer was dried with MgSO₄ and concentrated. The residue was purified by flash chromatography (25% ethyl acetate in normal-hexane) to obtain a hemiester (2b, 92% yield). According to the known method (H. Han, *Tetrahedron Lett.* 2004, 45, 3301-3304), it was determined to obtain an enantiomeric excess of 96% by reacting the hemiester and R-1-(1-naphthyl)ethyl amine to be converted to an ester amide corresponding to the hemiester. The enantioselectivity was measured using high performance liquid chromatography (Hypersil, 40:1, hexane:isopropyl alcohol, 1 mL/min., t (side product)=11.04 min., t (main product)=14.25 min.).

$^1$H NMR (300 MHz, CDCl₃) δ 2.32-2.65 (m, 4H), 3.02-3.12 (m, 2H), 3.69 (s, 3H), 5.68 (m, 2H); $^{13}$C NMR (75 MHz, CDCl₃) δ 25.68, 25.86, 39.58, 39.70, 52.10, 125.18, 125.30, 173.82, 179.66

Example 27

0.5 mmol of an anhydride (1b) was dissolved in 10 mL of methyl t-butyl ether at −20° C., 5 mol % of an organocatalyst (Q-BTBSA) was added thereto, 10 equivalents of methanol was added once thereto, and the mixture was stirred at −20° C. for 4 hours. This reaction was quenched using an aqueous solution of dilute hydrochloric acid (1N, 3 mL). The aqueous layer was extracted with ethyl acetate (2×10 mL), and the combined organic layer was dried with MgSO₄ and concentrated. The residue was purified by flash chromatography (25% ethyl acetate in normal-hexane) to obtain a hemiester (2b, 92% yield). According to the known method (H. Han, *Tetrahedron Lett.* 2004, 45, 3301-3304), it was determined to obtain an enantiomeric excess of 98% by reacting the hemiester and R-1-(1-naphthyl)ethyl amine to be converted to an ester amide corresponding to the hemiester. The enantioselectivity was measured using high performance liquid chromatography (Hypersil, 40:1, hexane:isopropyl alcohol, 1 mL/min., t (side product)=11.04 min., t (main product)=14.25 min.).

Example 28

0.5 mmol of an anhydride (1b) was dissolved in 10 mL of diisopropyl ether at −20° C., 5 mol % of an organocatalyst (Q-BTBSA) was added thereto, 10 equivalents of methanol was added once thereto, and the mixture was stirred at −20° C. for 5 hours. This reaction was quenched using an aqueous solution of dilute hydrochloric acid (1N, 3 mL). The aqueous layer was extracted with ethyl acetate (2×10 mL), and the combined organic layer was dried with MgSO$_4$ and concentrated. The residue was purified by flash chromatography (25% ethyl acetate in normal-hexane) to obtain a hemiester (2b, 92% yield). According to the known method (H. Han, *Tetrahedron Lett.* 2004, 45, 3301-3304), it was determined to obtain an enantiomeric excess of 99% by reacting the hemiester and R-1-(1-naphthyl)ethyl amine to be converted to an ester amide corresponding to the hemiester. The enantioselectivity was measured using high performance liquid chromatography (Hypersil, 40:1, hexane:isopropyl alcohol, 1 mL/min., t (side product)=11.04 min., t (main product)=14.25 min.).

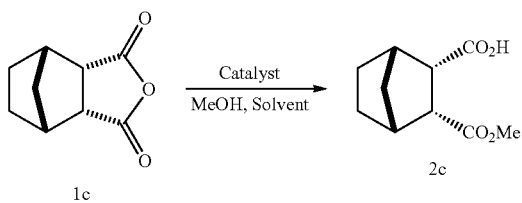

Example 29

0.5 mmol of an anhydride (1c) was dissolved in 5 mL of diethyl ether at 20° C., 5 mol % of an organo catalyst (Q-BTBSA) was added thereto, 10 equivalents of methanol was added once thereto, and the mixture was stirred at normal temperature for 4.5 hours. This reaction was quenched using an aqueous solution of dilute hydrochloric acid (1N, 3 mL). The aqueous layer was extracted with ethyl acetate (2×10 mL), and the combined organic layer was dried with MgSO$_4$ and concentrated. The residue was purified by flash chromatography (25% ethyl acetate in normal-hexane) to obtain a hemiester (2c, 90% yield). According to the known method (H. Han, *Tetrahedron Lett.* 2004, 45, 3301-3304), it was determined to obtain an enantiomeric excess of 96% by reacting the hemiester and R-1-(1-naphthyl)ethyl amine to be converted to an ester amide corresponding to the hemiester. The enantioselectivity was measured using high performance liquid chromatography (Hypersil, 40:1, hexane:isopropyl alcohol, 1 mL/min., t (side product)=12.27 min., t (main product)=20.35 min.).

$^1$H NMR (300 MHz, CDCl$_3$) δ 1.35-1.58 (m, 4H), 1.75-1.83 (m, 2H), 2.57-2.62 (m, 2H), 2.82-3.04 (m, 2H), 3.69 (s, 3H); $^{13}$C NMR (75 MHz, CDCl$_3$) δ 23.98, 24.17, 39.96, 40.22, 40.52, 46.83, 51.42, 172.98, 179.01

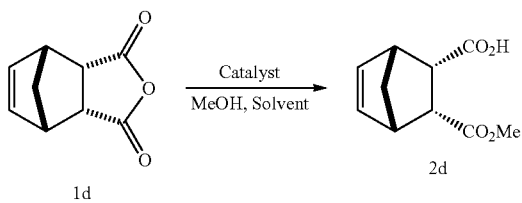

Example 30

0.5 mmol of an anhydride (1d) was dissolved in 5 mL of diethyl ether at 20° C., 5 mol % of an organocatalyst (Q-BTBSA) was added thereto, 10 equivalents of methanol was added once thereto, and the mixture was stirred at normal temperature for 5 hours. This reaction was quenched using an aqueous solution of dilute hydrochloric acid (1N, 3 mL). The aqueous layer was extracted with ethyl acetate (2×10 mL), and the combined organic layer was dried with MgSO$_4$ and concentrated. The residue was purified by flash chromatography (25% ethyl acetate in normal-hexane) to obtain a hemiester (2d, 90% yield). According to the known method (H. Han, *Tetrahedron Lett.* 2004, 45, 3301-3304), it was determined to obtain an enantiomeric excess of 94% by reacting the hemiester and R-1-(1-naphthyl)ethyl amine to be converted to an ester amide corresponding to the hemiester. The enantioselectivity was measured using high performance liquid chromatography (Hypersil, 40:1, hexane:isopropyl alcohol, 1 mL/min., t (side product)=18.90 min., t (main product)=24.93 min.).

$^1$H NMR (300 MHz, CDCl$_3$) δ 1.34 (bd, J=9.0 Hz, 1H), 1.50 (dt, J=9.0 Hz and 1.8 Hz, 1H), 3.01-3.41 (m, 4H), 3.59 (s, 3H), 6.21 (dd, J=5.0 and 3.0 Hz, 1H), 6.33 (dd, J=5.0 and 3.0 Hz, 1H); $^{13}$C NMR (75 MHz, CDCl$_3$) δ 46.23, 46.72, 48.08, 48.37, 48.93, 51.67, 134.46, 135.71, 173.00, 178.15.

Example 31

0.5 mmol of an anhydride (1d) was dissolved in 10 mL of diisopropyl ether at 20° C., 5 mol % of an organocatalyst (Q-BTBSA) was added thereto, 10 equivalents of methanol was added once thereto, and the mixture was stirred at normal temperature for 5 hours. This reaction was quenched using an aqueous solution of dilute hydrochloric acid (1N, 3 mL). The aqueous layer was extracted with ethyl acetate (2×10 mL), and the combined organic layer was dried with MgSO$_4$ and concentrated. The residue was purified by flash chromatography (25% ethyl acetate in normal-hexane) to obtain a hemiester (2d, 90% yield). According to the known method (H. Han, *Tetrahedron Lett.* 2004, 45, 3301-3304), it was determined to obtain an enantiomeric excess of 97.5% by reacting the hemiester and R-1-(1-naphthyl)ethyl amine to be converted to an ester amide corresponding to the hemiester. The enantioselectivity was measured using high performance liquid chromatography (Hypersil, 40:1, hexane:isopropyl alcohol, 1 mL/min., t (side product)=18.90 min., t (main product)=24.93 min).

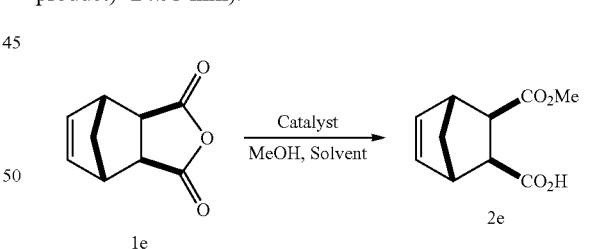

Example 32

0.5 mmol of an anhydride (1e) was dissolved in 5 mL of diethyl ether at 20° C., 5 mol % of an organo catalyst (Q-BTBSA) was added thereto, 10 equivalents of methanol was added once thereto, and the mixture was stirred at normal temperature for 6 hours. This reaction was quenched using an aqueous solution of dilute hydrochloric acid (1N, 3 mL). The aqueous layer was extracted with ethyl acetate (2×10 mL), and the combined organic layer was dried with MgSO$_4$ and concentrated. The residue was purified by flash chromatography (25% ethyl acetate in normal-hexane) to obtain a hemiester (2e, 88% yield). According to the known method (H. Han, *Tetrahedron Lett.* 2004, 45, 3301-3304), it was determined to obtain an enantiomeric excess of 95% by reacting the hemiester and R-1-(1-naphthyl)ethyl amine to be converted to an ester amide corresponding to the hemiester. The enantioselectivity was measured using high performance liquid chromatography (Hypersil, 40:1, hexane:isopropyl alcohol, 1 mL/min., t (side product)=10.86 min., t (main product)=11.31 min.).

$^1$H NMR (300 MHz, CDCl$_3$) δ 1.42 (bd, J=9.0 Hz, 1H), 2.13 (bd, J=9.0 Hz, 1H), 2.62 (m, 2H), 3.09 (m, 2H), 3.65 (s, 3H), 6.22 (m, 2H); $^{13}$C NMR (75 MHz, CDCl$_3$) δ 45.49, 45.52, 45.90, 47.47, 47.57, 51.97, 138.00, 138.19, 174.00, 180.13.

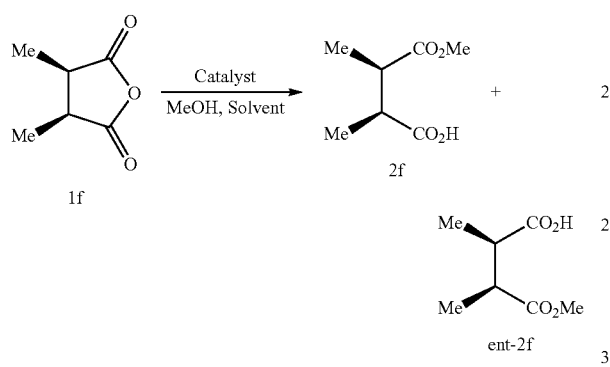

Example 33

0.5 mmol of an anhydride (1f) was dissolved in 20 mL, of methyl t-butyl ether at –20° C., 5 mol % of an organocatalyst (Q-BTBSA) was added thereto, 10 equivalents of methanol was added once thereto, and the mixture was stirred at –20° C. for 5 hours. This reaction was quenched using an aqueous solution of dilute hydrochloric acid (1N, 3 mL). The aqueous layer was extracted with ethyl acetate (2×10 mL), and the combined organic layer was dried with MgSO$_4$ and concentrated. The residue was purified by flash chromatography (25% ethyl acetate in normal-hexane) to obtain a hemiester (2f, 95% yield). According to the known method (H. Han, *Tetrahedron Lett.* 2004, 45, 3301-3304), it was determined to obtain an enantiomeric excess of 98% by reacting the hemiester and R-1-(1-naphthyl)ethyl amine to be converted to an ester amide corresponding to the hemiester. The enantioselectivity was measured using high performance liquid chromatography (Hypersil, 40:1, hexane:isopropyl alcohol, 1 mL/min., t (side product)=15.0 min., t (main product)=11.0 min.).

$^1$H NMR (300 MHz, CDCl$_3$) δ 1.02-1.21 (m, 6H), 2.71-2.79 (m, 2H), 3.66 (s, 3H); $^{13}$C NMR (75 MHz, CDCl$_3$) δ 14.8, 14.9, 42.3, 42.4, 52.0, 175.2, 180.3

Example 34

0.5 mmol of an anhydride (1f) was dissolved in 50 mL of diisopropyl ether at –20° C., 5 mol % of an organocatalyst (Q-BTBSA) was added thereto, 10 equivalents of methanol was added once thereto, and the mixture was stirred at –20° C. for 9 hours. This reaction was quenched using an aqueous solution of dilute hydrochloric acid (1N, 3 mL). The aqueous layer was extracted with ethyl acetate (2×10 mL), and the combined organic layer was dried with MgSO$_4$ and concentrated. The residue was purified by flash chromatography (25% ethyl acetate in normal-hexane) to obtain a hemiester (ent-2f, 99% yield). According to the known method (H. Han, *Tetrahedron Lett.* 2004, 45, 3301-3304), it was determined to obtain an enantiomeric excess of 99% by reacting the hemiester and R-1-(1-naphthyl)ethyl amine to be converted to an ester amide corresponding to the hemiester. The enantioselectivity was measured using high performance liquid chromatography (Hypersil, 40:1, hexane:isopropyl alcohol, 1 mL/min., t (side product)=11.0 min., t (main product)=15.0 min.).

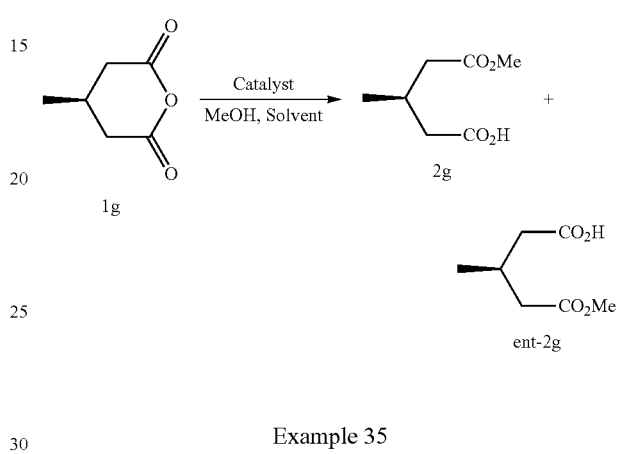

Example 35

0.5 mmol of an anhydride (1 g) was dissolved in 5 mL of methyl t-butyl ether at –20° C., 10 mol % of an organocatalyst (Q-BTBSA) was added thereto, 10 equivalents of methanol was added once thereto, and the mixture was stirred at –20° C. for 4 hours. This reaction was quenched using an aqueous solution of dilute hydrochloric acid (1N, 3 mL). The aqueous layer was extracted with ethyl acetate (2×10 mL), and the combined organic layer was dried with MgSO$_4$ and concentrated. The residue was purified by flash chromatography (25% ethyl acetate in normal-hexane) to obtain a hemiester (2 g, 95% yield). According to the known method (H. Han, *Tetrahedron Lett.* 2004, 45, 3301-3304), it was determined to obtain an enantiomeric excess of 91% by reacting the hemiester and R-1-(1-naphthyl)ethyl amine to be converted to an ester amide corresponding to the hemiester. The enantioselectivity was measured using high performance liquid chromatography (Hypersil, 40:1, hexane:isopropyl alcohol, 1 mL/min., t (side product)=33.5 min., t (main product)=30.3 min)

$^1$H NMR (300 MHz, CDCl$_3$) δ 1.05 (d, J=6.3 Hz, 3H), 2.2-2.6 (m, 5H), 3.68 (s, 3H); $^{13}$C NMR (75 MHz, CDCl$_3$) δ 19.9, 27.2, 40.6, 40.6, 51.7, 172.9, 178.8.

Example 36

0.5 mmol of an anhydride (1 g) was dissolved in 10 mL of diisopropyl ether at –20° C., 5 mol % of an organocatalyst (Q-BTBSA) was added thereto, 10 equivalents of methanol was added once thereto, and the mixture was stirred at –20° C. for 5 hours. This reaction was quenched using an aqueous solution of dilute hydrochloric acid (1N, 3 mL). The aqueous layer was extracted with ethyl acetate (2×10 mL), and the combined organic layer was dried with MgSO$_4$ and concentrated. The residue was purified by flash chromatography (25% ethyl acetate in normal-hexane) to obtain a hemiester (ent-2 g, 95% yield). According to the known method (H.

Han, *Tetrahedron Lett.* 2004, 45, 3301-3304), it was determined to obtain an enantiomeric excess of 87% by reacting the hemiester and R-1-(1-naphthyl)ethyl amine to be converted to an ester amide corresponding to the hemiester. The enantioselectivity was measured using high performance liquid chromatography (Hypersil, 40:1, hexane:isopropyl alcohol, 1 mL/min., t (side product)=30.3 min., t (main product)= 33.5 min.).

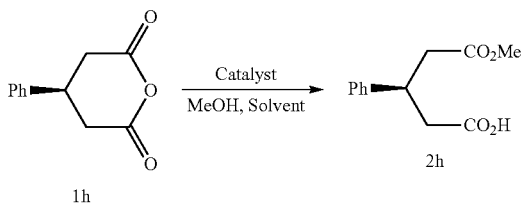

Example 37

0.5 mmol of an anhydride (1 h) was dissolved in 15 mL of methyl t-butyl ether at −20° C., 10 mol % of an organocatalyst (Q-BTBSA) was added thereto, 10 equivalents of methanol was added once thereto, and the mixture was stirred at −20° C. for 4 hours. This reaction was quenched using an aqueous solution of dilute hydrochloric acid (1N, 3 mL). The aqueous layer was extracted with ethyl acetate (2×10 mL), and the combined organic layer was dried with MgSO$_4$ and concentrated. The residue was purified by flash chromatography (25% ethyl acetate in normal-hexane) to obtain a hemiester (2 h, 97% yield). According to the known method (H. Han, *Tetrahedron Lett.* 2004, 45, 3301-3304), it was determined to obtain an enantiomeric excess of 94% by reacting the hemiester and R-1-(1-naphthyl)ethyl amine to be converted to an ester amide corresponding to the hemiester. The enantioselectivity was measured using high performance liquid chromatography (Hypersil, 40:1, hexane:isopropyl alcohol, 1 mL/min., t (side product)=24.1 min., t (main product)=12.1 min).

$^1$H NMR (300 MHz, CDCl$_3$) δ 2.6-2.8 (m, 4H), 3.56 (s, 3H), 3.58-3.67 (m, 1H), 7.10-7.35 (m, 5H); $^{13}$C NMR (75 MHz, CDCl$_3$) δ 37.9, 40.2, 40.5, 51.7, 127.1, 127.2, 128.7, 142.3, 172.2, 177.8

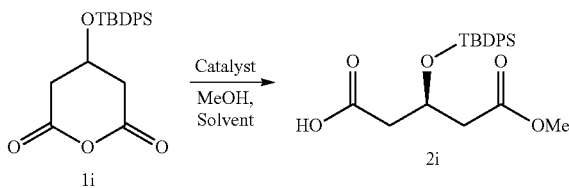

Example 38

0.5 mmol of an anhydride (11) was dissolved in 10 mL of methyl t-butyl ether at 20° C., 10 mol % of an organocatalyst (Q-BTBSA) was added thereto, 10 equivalents of methanol was added once thereto, and the mixture was stirred at 20° C. for 4 hours. This reaction was quenched using an aqueous solution of dilute hydrochloric acid (1N, 3 mL). The aqueous layer was extracted with ethyl acetate (2×10 mL), and the combined organic layer was dried with MgSO$_4$ and concentrated. The residue was purified by flash chromatography (25% ethyl acetate in normal-hexane) to obtain a hemiester (4 h, 97% yield). According to the known method (H. Han, *Tetrahedron Lett.* 2004, 45, 3301-3304), it was determined to obtain an enantiomeric excess of 92% by reacting the hemiester and R-1-(1-naphthyl)ethyl amine to be converted to an ester amide corresponding to the hemiester. The enantioselectivity was measured using high performance liquid chromatography (Hypersil, 98.5:1.5, hexane:isopropyl alcohol, 0.5 mL/min., t (main product)=21.3 min., t (side product)=23.3 min).

$^1$H NMR (300 MHz, CDCl$_3$) δ 1.04 (s, 9H), 2.54-2.70 (m, 4H), 3.57 (s, 3H), 4.50-4.58 (m, J=6.1 Hz, 1H), 7.35-7.45 (m, 6H), 7.68-7.70 (m, 4H); $^{13}$C NMR (75 MHz, CDCl$_3$) δ 19.14, 26.72, 41.40, 51.51, 66.81, 127.58, 129.78, 133.09, 133.20, 135.75, 135.77, 171.08, 177.02

Example 39

0.5 mmol of an anhydride (11) was dissolved in 10 mL of methyl t-butyl ether at 20° C., 10 mol % of an organocatalyst (HQ-BTBSA) was added thereto, 10 equivalents of methanol was added once thereto, and the mixture was stirred at 20° C. for 4 hours. This reaction was quenched using an aqueous solution of dilute hydrochloric acid (1N, 3 mL). The aqueous layer was extracted with ethyl acetate (2×10 mL), and the combined organic layer was dried with MgSO$_4$ and concentrated. The residue was purified by flash chromatography (25% ethyl acetate in normal-hexane) to obtain a hemiester (4 h, 96% yield). According to the known method (H. Han, *Tetrahedron Lett.* 2004, 45, 3301-3304), it was determined to obtain an enantiomeric excess of 92% by reacting the hemiester and R-1-(1-naphthyl)ethyl amine to be converted to an ester amide corresponding to the hemiester. The enantioselectivity was measured using high performance liquid chromatography (Hypersil, 98.5:1.5, hexane:isopropyl alcohol, 0.5 mL/min., t (main product)=21.3 min., t (side product)=23.3 min.).

Example 40

0.5 mmol of an anhydride (1i) was dissolved in 10 mL of methyl t-butyl ether at 20° C., 10 mol % of an organocatalyst (CD-BTBSA) was added thereto, 10 equivalents of methanol was added once thereto, and the mixture was stirred at 20° C. for 4 hours. This reaction was quenched using an aqueous solution of dilute hydrochloric acid (1N, 3 mL). The aqueous layer was extracted with ethyl acetate (2×10 mL), and the combined organic layer was dried with MgSO$_4$ and concentrated. The residue was purified by flash chromatography (25% ethyl acetate in normal-hexane) to obtain a hemiester (4 h, 94% yield). According to the known method (H. Han, *Tetrahedron Lett.* 2004, 45, 3301-3304), it was determined to obtain an enantiomeric excess of 93% by reacting the hemiester and R-1-(1-naphthyl)ethyl amine to be converted to an ester amide corresponding to the hemiester. The enantioselectivity was measured using high performance liquid chromatography (Hypersil, 98.5:1.5, hexane:isopropyl alcohol, 0.5 mL/min., t (main product)=21.3 min., t (side product) =23.3 min.).

Example 41

0.5 mmol of an anhydride (11) was dissolved in 10 mL of methyl t-butyl ether at 20° C., 10 mol % of an organocatalyst (HCD-BTBSA) was added thereto, 10 equivalents of methanol was added once thereto, and the mixture was stirred at 20°

C. for 3 hours. This reaction was quenched using an aqueous solution of dilute hydrochloric acid (1N, 3 mL). The aqueous layer was extracted with ethyl acetate (2×10 mL), and the combined organic layer was dried with MgSO$_4$ and concentrated. The residue was purified by flash chromatography (25% ethyl acetate in normal-hexane) to obtain a hemiester (3 h, 94% yield). According to the known method (H. Han, *Tetrahedron Lett.* 2004, 45, 3301-3304), it was determined to obtain an enantiomeric excess of 92% by reacting the hemiester and R-1-(1-naphthyl)ethyl amine to be converted to an ester amide corresponding to the hemiester. The enantioselectivity was measured using high performance liquid chromatography (Hypersil, 98.5:1.5, hexane:isopropyl alcohol, 0.5, mL/min., t (main product)=21.3 min., t (side product)=23.3 min.).

Example 42

0.5 mmol of an anhydride (1l) was dissolved in 10 mL, of methyl t-butyl ether at 20° C., 10 mol % of an organocatalyst (Q-PTSA) was added thereto, 10 equivalents of methanol was added once thereto, and the mixture was stirred at 20° C. for 8 hours. This reaction was quenched using an aqueous solution of dilute hydrochloric acid (1N, 3 mL). The aqueous layer was extracted with ethyl acetate (2×10 mL), and the combined organic layer was dried with MgSO$_4$ and concentrated. The residue was purified by flash chromatography (25% ethyl acetate in normal-hexane) to obtain a hemiester (8 h, 89% yield). According to the known method (H. Han, *Tetrahedron Lett.* 2004, 45, 3301-3304), it was determined to obtain an enantiomeric excess of 91% by reacting the hemiester and R-1-(1-naphthyl)ethyl amine to be converted to an ester amide corresponding to the hemiester. The enantioselectivity was measured using high performance liquid chromatography (Hypersil, 98.5:1.5, hexane:isopropyl alcohol, 0.5 mL/min., t (main product)=21.3 min., t (side product)=23.3 min.).

Example 43

0.5 mmol of an anhydride (1l) was dissolved in 10 mL of methyl t-butyl ether at 20° C., 10 mol % of an organocatalyst (Q-OTSA) was added thereto, 10 equivalents of methanol was added once thereto, and the mixture was stirred at 20° C. for 8 hours. This reaction was quenched using an aqueous solution of dilute hydrochloric acid (1N, 3 mL). The aqueous layer was extracted with ethyl acetate (2×10 mL), and the combined organic layer was dried with MgSO$_4$ and concentrated. The residue was purified by flash chromatography (25% ethyl acetate in normal-hexane) to obtain a hemiester (8 h, 96% yield). According to the known method (H. Han, *Tetrahedron Lett.* 2004, 45, 3301-3304), it was determined to obtain an enantiomeric excess of 90% by reacting the hemiester and R-1-(1-naphthyl)ethyl amine to be converted to an ester amide corresponding to the hemiester. The enantioselectivity was measured using high performance liquid chromatography (Hypersil, 98.5:1.5, hexane:isopropyl alcohol, 0.5 mL/min., t (main product)=21.3 min., t (side product)=23.3 min.).

Example 44

0.5 mmol of an anhydride (1i) was dissolved in 10 mL of methyl t-butyl ether at 20° C., 10 mol % of an organocatalyst (Q-MTSA) was added thereto, 10 equivalents of methanol was added once thereto, and the mixture was stirred at 20° C. for 8 hours. This reaction was quenched using an aqueous solution of dilute hydrochloric acid (1N, 3 mL). The aqueous layer was extracted with ethyl acetate (2×10 mL), and the combined organic layer was dried with MgSO$_4$ and concentrated. The residue was purified by flash chromatography (25% ethyl acetate in normal-hexane) to obtain a hemiester (8 h, 99% yield). According to the known method (H. Han, *Tetrahedron Lett.* 2004, 45, 3301-3304), it was determined to obtain an enantiomeric excess of 91% by reacting the hemiester and R-1-(1-naphthyl)ethyl amine to be converted to an ester amide corresponding to the hemiester. The enantioselectivity was measured using high performance liquid chromatography (Hypersil, 98.5:1.5, hexane:isopropyl alcohol, 0.5 mL/min., t (main product)=21.3 min., t (side product)=23.3 min.).

Example 45

0.5 mmol of an anhydride (1i) was dissolved in 10 mL of methyl t-butyl ether at 20° C., 10 mol % of an organocatalyst (Q-1-NSA) was added thereto, 10 equivalents of methanol was added once thereto, and the mixture was stirred at 20° C. for 12 hours. This reaction was quenched using an aqueous solution of dilute hydrochloric acid (1N, 3 mL). The aqueous layer was extracted with ethyl acetate (2×10 mL), and the combined organic layer was dried with MgSO$_4$ and concentrated. The residue was purified by flash chromatography (25% ethyl acetate in normal-hexane) to obtain a hemiester (12 h, 92% yield). According to the known method (H. Han, *Tetrahedron Lett.* 2004, 45, 3301-3304), it was determined to obtain an enantiomeric excess of 90% by reacting the hemiester and R-1-(1-naphthyl)ethyl amine to be converted to an ester amide corresponding to the hemiester. The enantioselectivity was measured using high performance liquid chromatography (Hypersil, 98.5:1.5, hexane:isopropyl alcohol, 0.5 mL/min., t (main product)=21.3 min., t (side product)=23.3 min.).

Example 46

0.5 mmol of an anhydride (1l) was dissolved in 10 mL of methyl t-butyl ether at 20° C., 10 mol % of an organocatalyst (Q-2-NSA) was added thereto, 10 equivalents of methanol was added once thereto, and the mixture was stirred at 20° C. for 6 hours. This reaction was quenched using an aqueous solution of dilute hydrochloric acid (1N, 3 mL). The aqueous layer was extracted with ethyl acetate (2×10 mL), and the combined organic layer was dried with MgSO$_4$ and concentrated. The residue was purified by flash chromatography (25% ethyl acetate in normal-hexane) to obtain a hemiester (6 h, 91% yield). According to the known method (H. Han, *Tetrahedron Lett.* 2004, 45, 3301-3304), it was determined to obtain an enantiomeric excess of 91% by reacting the hemiester and R-1-(1-naphthyl)ethyl amine to be converted to an ester amide corresponding to the hemiester. The enantioselectivity was measured using high performance liquid chromatography (Hypersil, 98.5:1.5, hexane:isopropyl alcohol, 0.5 mL/min., t (main product)=21.3 min., t (side product)=23.3 min.).

Example 47

0.5 mmol of an anhydride (1l) was dissolved in 10 mL, of methyl t-butyl ether at 20° C., 10 mol % of an organocatalyst (Q-BSA) was added thereto, 10 equivalents of methanol was added once thereto, and the mixture was stirred at 20° C. for 8 hours. This reaction was quenched using an aqueous solution of dilute hydrochloric acid (1N, 3 mL). The aqueous layer was extracted with ethyl acetate (2×10 mL), and the combined organic layer was dried with MgSO$_4$ and concentrated. The residue was purified by flash chromatography (25% ethyl acetate in normal-hexane) to obtain a hemiester (8 h, 96% yield). According to the known method (H. Han, *Tetrahedron Lett.* 2004, 45, 3301-3304), it was determined to obtain an enantiomeric excess of 91% by reacting the hemiester and R-1-(1-naphthyl)ethyl amine to be converted to an ester amide corresponding to the hemiester. The enantioselectivity was measured using high performance liquid chromatography (Hypersil, 98.5:1.5, hexane:isopropyl alcohol, 0.5 mL/min., t (main product)=21.3 min., t (side product)=23.3 min.).

Example 48

0.5 mmol of an anhydride (1i) was dissolved in 10 mL, of methyl t-butyl ether at 20° C., 10 mol % of an organocatalyst (Q-MXSA) was added thereto, 10 equivalents of methanol was added once thereto, and the mixture was stirred at 20° C. for 7 hours. This reaction was quenched using an aqueous solution of dilute hydrochloric acid (1N, 3 mL). The aqueous layer was extracted with ethyl acetate (2×10 mL), and the combined organic layer was dried with MgSO$_4$ and concentrated. The residue was purified by flash chromatography (25% ethyl acetate in normal-hexane) to obtain a hemiester (7 h, 87% yield). According to the known method (H. Han, *Tetrahedron Lett.* 2004, 45, 3301-3304), it was determined to obtain an enantiomeric excess of 91% by reacting the hemiester and R-1-(1-naphthyl)ethyl amine to be converted to an ester amide corresponding to the hemiester. The enantioselectivity was measured using high performance liquid chromatography (Hypersil, 98.5:1.5, hexane:isopropyl alcohol, 0.5 mL/min., t (main product)=21.3 min., t (side product)=23.3 min.).

Example 49

0.5 mmol of an anhydride (1i) was dissolved in 10 mL, of methyl t-butyl ether at 0° C., 10 mol % of an organocatalyst (Q-BTBSA) was added thereto, 10 equivalents of methanol was added once thereto, and the mixture was stirred at 0° C. for 11 hours. This reaction was quenched using an aqueous solution of dilute hydrochloric acid (1N, 3 mL). The aqueous layer was extracted with ethyl acetate (2×10 mL), and the combined organic layer was dried with MgSO$_4$ and concentrated. The residue was purified by flash chromatography (25% ethyl acetate in normal-hexane) to obtain a hemiester (11 h, 96% yield). According to the known method (H. Han, *Tetrahedron Lett.* 2004, 45, 3301-3304), it was determined to obtain an enantiomeric excess of 95% by reacting the hemiester and R-1-(1-naphthyl)ethyl amine to be converted to an ester amide corresponding to the hemiester. The enantioselectivity was measured using high performance liquid chromatography (Hypersil, 98.5:1.5, hexane:isopropyl alcohol, 0.5 mL/min., t (main product)=21.3 min., t (side product)=23.3 min.).

Example 50

0.5 mmol of an anhydride (1i) was dissolved in 10 mL, of methyl t-butyl ether at −20° C., 10 mol % of an organocatalyst (Q-BTBSA) was added thereto, 10 equivalents of methanol was added once thereto, and the mixture was stirred at −20° C. for 28 hours. This reaction was quenched using an aqueous solution of dilute hydrochloric acid (1N, 3 mL). The aqueous layer was extracted with ethyl acetate (2×10 mL), and the combined organic layer was dried with MgSO$_4$ and concentrated. The residue was purified by flash chromatography (25% ethyl acetate in normal-hexane) to obtain a hemiester (28 h, 87% yield). According to the known method (H. Han, *Tetrahedron Lett.* 2004, 45, 3301-3304), it was determined to obtain an enantiomeric excess of 96% by reacting the hemiester and R-1-(1-naphthyl)ethyl amine to be converted to an ester amide corresponding to the hemiester. The enantioselectivity was measured using high performance liquid chromatography (Hypersil, 98.5:1.5, hexane:isopropyl alcohol, 0.5 mL/min., t (main product)=21.3 min., t (side product)=23.3 min.).

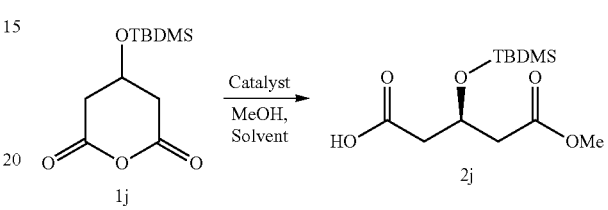

Example 51

0.5 mmol of an anhydride (1j) was dissolved in 10 mL of methyl t-butyl ether at 0° C., 10 mol % of an organocatalyst (Q-BTBSA) was added thereto, 10 equivalents of methanol was added once thereto, and the mixture was stirred at 0° C. for 11 hours. This reaction was quenched using an aqueous solution of dilute hydrochloric acid (1N, 3 mL). The aqueous layer was extracted with ethyl acetate (2×10 mL), and the combined organic layer was dried with MgSO$_4$ and concentrated. The residue was purified by flash chromatography (25% ethyl acetate in normal-hexane) to obtain a hemiester (11 h, 97% yield). According to the known method (H. Han, *Tetrahedron Lett.* 2004, 45, 3301-3304), it was determined to obtain an enantiomeric excess of 92% by reacting the hemiester and R-1-(1-naphthyl)ethyl amine to be converted to an ester amide corresponding to the hemiester. The enantioselectivity was measured using high performance liquid chromatography (Hypersil, 40:1, hexane:isopropyl alcohol, 1 mL/min., t (main product)=7.6 min., t (side product)=11.9 min.).

$^1$H NMR (300 MHz, CDCl$_3$) δ 0.50-0.60 (d, J=2.7 Hz, 6H), 0.83 (s, 9H), 2.52-2.66 (m, 4H), 3.67 (s, 3H), 4.50-4.58 (m, J=6.2 Hz, 1H); $^{13}$C NMR (75 MHz, CDCl$_3$) δ−5.02, −5.01, 17.81, 25.55, 42.17, 42.22, 51.62, 66.02, 171.36, 177.13

Example 52

0.5 mmol of an anhydride (1j) was dissolved in 10 mL of methyl t-butyl ether at −20° C., 10 mol % of an organocatalyst (Q-BTBSA) was added thereto, 10 equivalents of methanol was added once thereto, and the mixture was stirred at −20° C. for 28 hours. This reaction was quenched using an aqueous solution of dilute hydrochloric acid (1N, 3 mL). The aqueous layer was extracted with ethyl acetate (2×10 mL), and the combined organic layer was dried with MgSO$_4$ and concentrated. The residue was purified by flash chromatography (25% ethyl acetate in normal-hexane) to obtain a hemiester (28 h, 98% yield). According to the known method (H. Han, *Tetrahedron Lett.* 2004, 45, 3301-3304), it was determined to obtain an enantiomeric excess of 93% by reacting the hemiester and R-1-(1-naphthyl)ethyl amine to be converted to an ester amide corresponding to the hemiester. The enan-

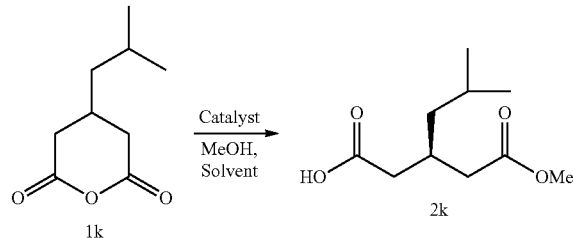

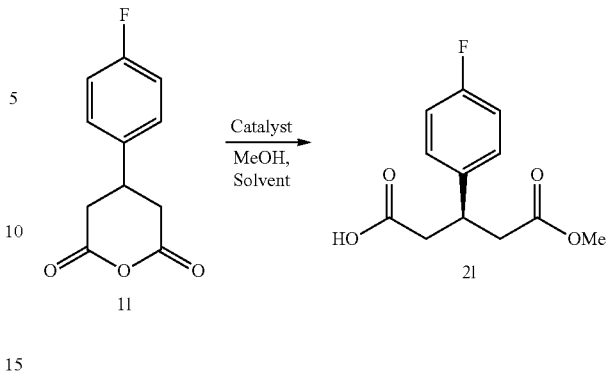

Example 55

Example 53

0.5 mmol of an anhydride (1 k) was dissolved in 10 mL of methyl t-butyl ether at 0° C., 10 mol % of an organocatalyst (Q-BTBSA) was added thereto, 10 equivalents of methanol was added once thereto, and the mixture was stirred at 0° C. for 6 hours. This reaction was quenched using an aqueous solution of dilute hydrochloric acid (1N, 3 The aqueous layer was extracted with ethyl acetate (2×10 mL), and the combined organic layer was dried with MgSO$_4$ and concentrated. The residue was purified by flash chromatography (25% ethyl acetate in normal-hexane) to obtain a hemiester (6 h, 95% yield). According to the known method (H. Han, *Tetrahedron Lett.* 2004, 45, 3301-3304), it was determined to obtain an enantiomeric excess of 91% by reacting the hemiester and R-1-(1-naphthyl)ethyl amine to be converted to an ester amide corresponding to the hemiester. The enantioselectivity was measured using high performance liquid chromatography (Hypersil, 40:1, hexane:isopropyl alcohol, 1 mL/min., t (main product)=11.4 min., t (side product)=16.2 min.)

$^1$H NMR (300 MHz, CDCl$_3$) δ 0.86-0.88 (d, J=6.6 Hz, 6H), 1.18-1.21 (m, 2H), 1.53-1.67 (m, 1H), 2.36-2.37 (m, 5H), 3.65 (s, 3H); $^{13}$C NMR (75 MHz, CDCl$_3$) δ 22.49, 25.15, 29.70, 38.39, 43.37, 51.50, 173.02, 178.91

Example 54

0.5 mmol of an anhydride (1 k) was dissolved in 10 mL of methyl t-butyl ether at −20° C., 10 mol % of an organocatalyst (Q-BTBSA) was added thereto, 10 equivalents of methanol was added once thereto, and the mixture was stirred at −20° C. for 14 hours. This reaction was quenched using an aqueous solution of dilute hydrochloric acid (1N, 3 mL). The aqueous layer was extracted with ethyl acetate (2×10 mL), and the combined organic layer was dried with MgSO$_4$ and concentrated. The residue was purified by flash chromatography (25% ethyl acetate in normal-hexane) to obtain a hemiester (14 h, 96% yield). According to the known method (H. Han, *Tetrahedron Lett.* 2004, 45, 3301-3304), it was determined to obtain an enantiomeric excess of 92% by reacting the hemiester and R-1-(1-naphthyl)ethyl amine to be converted to an ester amide corresponding to the hemiester. The enantioselectivity was measured using high performance liquid chromatography (Hypersil, 40:1, hexane:isopropyl alcohol, 1 mL/min., t (main product)=11.4 min., t (side product)=16.2 min.).

Example 55

0.5 mmol of an anhydride (11) was dissolved in 10 mL of methyl t-butyl ether at 20° C., 10 mol % of an organo catalyst (Q-BTBSA) was added thereto, 10 equivalents of methanol was added once thereto, and the mixture was stirred at 20° C. for 1 hours. This reaction was quenched using an aqueous solution of dilute hydrochloric acid (1N, 3 mL). The aqueous layer was extracted with ethyl acetate (2×10 mL), and the combined organic layer was dried with MgSO$_4$ and concentrated. The residue was purified by flash chromatography (25% ethyl acetate in normal-hexane) to obtain a hemiester (1 h, 92% yield). According to the known method (H. Han, *Tetrahedron Lett.* 2004, 45, 3301-3304), it was determined to obtain an enantiomeric excess of 91% by reacting the hemiester and R-1-(1-naphthyl)ethyl amine to be converted to an ester amide corresponding to the hemiester. The enantioselectivity was measured using high performance liquid chromatography (Kromasil, 90.5:9.5, hexane:isopropyl alcohol, 1 mL/min., t (main product)=9.1 min., t (side product)=16.1 min.).

$^1$H NMR (300 MHz, CDCl$_3$) δ 2.57-2.79 (m, 4H), 3.58-3.67 (m, 4H), 6.95-7.00 (m, 2H), 7.16-7.21 (m, 2H); $^{13}$C NMR (75 MHz, CDCl$_3$) δ 37.17, 40.23, 40.41, 51.66, 115.44 (d, J=21.3 Hz), 128.68 (d, J=8.0 Hz), 137.83 (d, J=3.2 Hz), 161.69 (d, J=245.3 Hz), 171.88, 177.53

Example 56

0.5 mmol of an anhydride (11) was dissolved in 10 mL of methyl t-butyl ether at −20° C., 10 mol % of an organocatalyst (Q-BTBSA) was added thereto, 10 equivalents of methanol was added once thereto, and the mixture was stirred at −20° C. for 19 hours. This reaction was quenched using an aqueous solution of dilute hydrochloric acid (1N, 3 mL). The aqueous layer was extracted with ethyl acetate (2×10 mL), and the combined organic layer was dried with MgSO$_4$ and concentrated. The residue was purified by flash chromatography (25% ethyl acetate in normal-hexane) to obtain a hemiester (19 h, 81% yield). According to the known method (H. Han, *Tetrahedron Lett.* 2004, 45, 3301-3304), it was determined to obtain an enantiomeric excess of 93% by reacting the hemiester and R-1-(1-naphthyl)ethyl amine to be converted to an ester amide corresponding to the hemiester. The enantioselectivity was measured using high performance liquid chromatography (Kromasil, 90.5:9.5, hexane:isopropyl alcohol, 1 mL/min., t (main product)=9.1 min., t (side product)=16.1 min.).

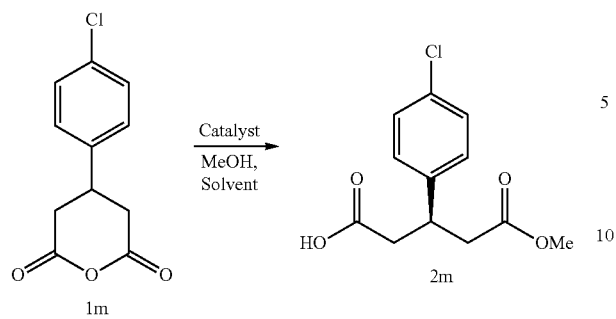

Example 57

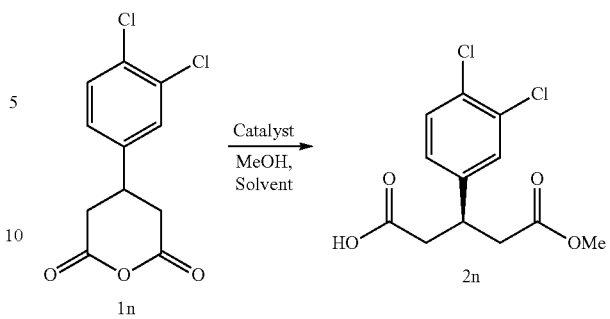

Example 59

0.5 mmol of an anhydride (1m) was dissolved in 10 mL of methyl t-butyl ether at 20° C., 10 mol % of an organocatalyst (Q-BTBSA) was added thereto, 10 equivalents of methanol was added once thereto, and the mixture was stirred at 20° C. for 1 hours. This reaction was quenched using an aqueous solution of dilute hydrochloric acid (1N, 3 mL). The aqueous layer was extracted with ethyl acetate (2×10 mL), and the combined organic layer was dried with MgSO$_4$ and concentrated. The residue was purified by flash chromatography (25% ethyl acetate in normal-hexane) to obtain a hemiester (1 h, 92% yield). According to the known method (H. Han, *Tetrahedron Lett.* 2004, 45, 3301-3304), it was determined to obtain an enantiomeric excess of 92% by reacting the hemiester and R-1-(1-naphthyl)ethyl amine to be converted to an ester amide corresponding to the hemiester. The enantioselectivity was measured using high performance liquid chromatography (Kromasil, 90.5:9.5, hexane:isopropyl alcohol, 1 mL/min., t (main product)=9.4 min., t (side product)=17.4 min.).

$^1$H NMR (300 MHz, CDCl$_3$) δ 2.56-2.78 (m, 4H), 3.55-3.65 (m, 4H), 7.13-7.16 (m, 2H), 7.24-7.27 (m, 2H); $^{13}$C NMR (75 MHz, CDCl$_3$) δ 37.25, 40.00, 40.19, 51.70, 128.56, 128.74, 132.71, 140.63, 171.80, 177.22

Example 58

0.5 mmol of an anhydride (1m) was dissolved in 10 mL of methyl t-butyl ether at −20° C., 10 mol % of an organocatalyst (Q-BTBSA) was added thereto, 10 equivalents of methanol was added once thereto, and the mixture was stirred at −20° C. for 18 hours. This reaction was quenched using an aqueous solution of dilute hydrochloric acid (1N, 3 mL) The aqueous layer was extracted with ethyl acetate (2×10 mL), and the combined organic layer was dried with MgSO$_4$ and concentrated. The residue was purified by flash chromatography (25% ethyl acetate in normal-hexane) to obtain a hemiester (18 h, 87% yield). According to the known method (H. Han, *Tetrahedron Lett.* 2004, 45, 3301-3304), it was determined to obtain an enantiomeric excess of 92% by reacting the hemiester and R-1-(1-naphthyl)ethyl amine to be converted to an ester amide corresponding to the hemiester. The enantioselectivity was measured using high performance liquid chromatography (Kromasil, 90.5:9.5, hexane:isopropyl alcohol, 1 mL/min., t (main product)=9.4 min., t (side product)=17.4 min.).

0.5 mmol of an anhydride (1m) was dissolved in 10 mL of methyl t-butyl ether at −20° C., 10 mol % of an organocatalyst (Q-BTBSA) was added thereto, 10 equivalents of methanol was added once thereto, and the mixture was stirred at −20° C. for 18 hours. This reaction was quenched using an aqueous solution of dilute hydrochloric acid (1N, 3 mL). The aqueous layer was extracted with ethyl acetate (2×10 mL), and the combined organic layer was dried with MgSO$_4$ and concentrated. The residue was purified by flash chromatography (25% ethyl acetate in normal-hexane) to obtain a hemiester (18 h, 87% yield). According to the known method (H. Han, *Tetrahedron Lett.* 2004, 45, 3301-3304), it was determined to obtain an enantiomeric excess of 92% by reacting the hemiester and R-1-(1-naphthyl)ethyl amine to be converted to an ester amide corresponding to the hemiester. The enantioselectivity was measured using high performance liquid chromatography (Kromasil, 90.5:9.5, hexane:isopropyl alcohol, 1 mL/min., t (main product)=9.2 min., t (side product)=17.1 min.).

$^1$H NMR (300 MHz, CDCl$_3$) δ 2.57-2.80 (m, 4H), 3.54-3.60 (m, 4H), 7.06-7.10 (m, 1H), 7.32-7.38 (m, 2H); $^{13}$C NMR (75 MHz, CDCl$_3$) δ 37.02, 39.76, 39.95, 51.81, 126.75, 129.28, 130.57, 131.06, 132.57, 142.46, 171.53, 177.09

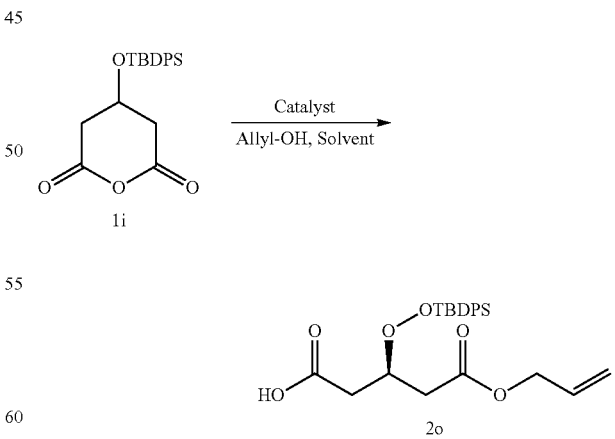

Example 60

0.5 mmol of an anhydride (1l) was dissolved in 10 mL, of methyl t-butyl ether at 20° C., 10 mol % of an organocatalyst (Q-BTBSA) was added thereto, 10 equivalents of allyl alcohol was added once thereto, and the mixture was stirred at 20° C. for 20 hours. This reaction was quenched using an aqueous solution of dilute hydrochloric acid (1N, 3 mL). The aqueous layer was extracted with ethyl acetate (2×10 mL), and the combined organic layer was dried with MgSO$_4$ and concentrated. The residue was purified by flash chromatography (25% ethyl acetate in normal-hexane) to obtain a hemiester (20 h, 92% yield). According to the known method (H. Han, *Tetrahedron Lett.* 2004, 45, 3301-3304), it was determined to obtain an enantiomeric excess of 91% by reacting the hemiester and R-1-(1-naphthyl)ethyl amine to be converted to an ester amide corresponding to the hemiester. The enantioselectivity was measured using high performance liquid chromatography (Kromasil, 99.2:0.8, hexane:isopropyl alcohol, 0.5 mL/min., t (main product)=32.6 min., t (side product)=35.9 min.).

$^1$H NMR (300 MHz, CDCl$_3$) δ 1.05 (s, 9H), 2.61-2.66 (m, 4H), 4.47-4.58 (m, 3H), 5.20-5.30 (m, 1H), 5.79-5.92 (m, 1H), 7.36-7.48 (m, 6H), 7.69-7.71 (d, J=6.3 Hz, 4H); $^{13}$C NMR (75 MHz, CDCl$_3$) δ 19.15, 26.74, 41.47, 65.17, 66.82, 118.34, 127.59, 129.80, 131.84, 133.07, 133.23, 135.77, 135.80, 170.29, 176.93

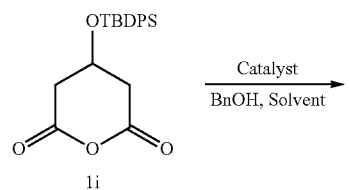

Example 61

0.5 mmol of an anhydride (1l) was dissolved in 10 mL, of methyl t-butyl ether at 20° C., 10 mol % of an organocatalyst (Q-BTBSA) was added thereto, 10 equivalents of benzyl alcohol was added once thereto, and the mixture was stirred at 20° C. for 8 hours. This reaction was quenched using an aqueous solution of dilute hydrochloric acid (1N, 3 mL). The aqueous layer was extracted with ethyl acetate (2×10 mL), and the combined organic layer was dried with MgSO$_4$ and concentrated. The residue was purified by flash chromatography (10% ethyl acetate in normal-hexane) to obtain a hemiester (8 h, 90% yield). According to the known method (H. Han, *Tetrahedron Lett.* 2004, 45, 3301-3304), it was determined to obtain an enantiomeric excess of 96% by reacting the hemiester and R-1-(1-naphthyl)ethyl amine to be converted to an ester amide corresponding to the hemiester. The enantioselectivity was measured using high performance liquid chromatography (Kromasil, 99.1:0.9, hexane:isopropyl alcohol, 0.5 mL/min., t (main product)=15.3 min., t (side product)=15.7 min.).

$^1$H NMR (300 MHz, CDCl$_3$) δ 1.01 (s, 9H), 2.53-2.71 (m, 4H-1), 4.48-4.56 (m, J=6.3 Hz, 1H), 4.94-5.06 (q, J=6.3 Hz, 2H), 7.24-7.46 (m, 11H), 7.64-7.67 (m, 4H-1); $^{13}$C NMR (75 MHz, CDCl$_3$) δ 19.16, 26.76, 41.32, 41.54, 66.32, 66.85, 127.62, 128.19, 128.49, 129.82, 133.03, 133.26, 135.59, 135.80, 135.82, 170.44, 176.79

Example 62

0.5 mmol of an anhydride (1l) was dissolved in 10 mL of methyl t-butyl ether at 0° C., 10 mol % of an organocatalyst (Q-BTBSA) was added thereto, 10 equivalents of benzyl alcohol was added once thereto, and the mixture was stirred at 0° C. for 15 hours. This reaction was quenched using an aqueous solution of dilute hydrochloric acid (1N, 3 mL). The aqueous layer was extracted with ethyl acetate (2×10 mL), and the combined organic layer was dried with MgSO$_4$ and concentrated. The residue was purified by flash chromatography (10% ethyl acetate in normal-hexane) to obtain a hemiester (15 h, 98% yield). According to the known method (H. Han, *Tetrahedron Lett.* 2004, 45, 3301-3304), it was determined to obtain an enantiomeric excess of 97% by reacting the hemiester and R-1-(1-naphthyl)ethyl amine to be converted to an ester amide corresponding to the hemiester. The enantioselectivity was measured using high performance liquid chromatography (Kromasil, 99.1:0.9, hexane:isopropyl alcohol, 0.5 mL/min., t (main product)=15.3 min., t (side product)=15.7 min.).

Example 63

0.5 mmol of an anhydride (1i) was dissolved in 10 mL of methyl t-butyl ether at −20° C., 10 mol % of an organocatalyst (Q-BTBSA) was added thereto, 10 equivalents of benzyl alcohol was added once thereto, and the mixture was stirred at −20° C. for 4.5 days. This reaction was quenched using an aqueous solution of dilute hydrochloric acid (1N, 3 mL). The aqueous layer was extracted with ethyl acetate (2×10 mL), and the combined organic layer was dried with MgSO$_4$ and concentrated. The residue was purified by flash chromatography (10% ethyl acetate in normal-hexane) to obtain a hemiester (4.5d, 93% yield). According to the known method (H. Han, *Tetrahedron Lett.* 2004, 45, 3301-3304), it was determined to obtain an enantiomeric excess of 98% by reacting the hemiester and R-1-(1-naphthyl)ethyl amine to be converted to an ester amide corresponding to the hemiester. The enantioselectivity was measured using high performance liquid chromatography (Kromasil, 99.1:0.9, hexane:isopropyl alcohol, 0.5 mL/min., t (main product)=15.3 min., t (side product)=15.7 min.).

Table 1 below represents yields and enantioselectivities about each desymmetrization in Examples 15 to 63.

TABLE 1

| Example | Cyclic Anhydride | Product | Solvent (mL) | Catalyst (mol %) | Temper (° C.) | Hour | Yield (%) | % ee |
|---|---|---|---|---|---|---|---|---|
| 15 | 1a | 2a | Et$_2$O (5 mL) | Q-BTBSA (10 mol %) | 20 | 1 | 91 | 96 |
| 16 | 1a | 2a | Et$_2$O (5 mL) | Q-BTBSA (5 mol %) | 20 | 2 | 92 | 95 |
| 17 | 1a | 2a | Et$_2$O (5 mL) | Q-BTBSA (1 mol %) | 20 | 6 | 92 | 95 |
| 18 | 1a | 2a | Et$_2$O (5 mL) | Q-BTBSA (0.5 mol %) | 20 | 20 | 89 | 93 |
| 19 | 1a | 2a | Et$_2$O (5 mL) | Q-PTSA (10 mol %) | 20 | 20 | 95 | 92 |
| 20 | 1a | 2a | Et$_2$O (5 mL) | Q-1-NSA (5 mol %) | 20 | 1 | 95 | 92 |
| 21 | 1a | 2a | Et$_2$O (5 mL) | Q-2-NSA (5 mol %) | 20 | 1 | 95 | 92 |

TABLE 1-continued

| Example | Cyclic Anhydride | Product | Solvent (mL) | Catalyst (mol %) | Temper (° C.) | Hour | Yield (%) | % ee |
|---|---|---|---|---|---|---|---|---|
| 22 | 1a | 2a | IPr$_2$O (5 mL) | Q-BSA (5 mol %) | 20 | 1.5 | 99 | 96 |
| 23 | 1a | 2a | MTBE (5 mL) | Q-4-VBSA (5 mol %) | 20 | 4 | 99 | 95 |
| 24 | 1a | 2a | IPr$_2$O (5 mL) | Q-4-VBSA (5 mol %) | 20 | 1.5 | 99 | 95 |
| 25 | 1a | 2a | IPr$_2$O (10 mL) | Q-4-VBSA (5 mol %) | −20 | 4 | 99 | 97 |
| 26 | 1b | 2b | Et$_2$O (5 mL) | Q-BTBSA (5 mol %) | 20 | 5 | 92 | 96 |
| 27 | 1b | 2b | MTBE (10 mL) | Q-BTBSA (5 mol %) | −20 | 4.5 | 92 | 98 |
| 28 | 1b | 2b | IPr$_2$O (10 mL) | Q-BTBSA (5 mol %) | −20 | 5 | 92 | 99 |

TABLE 1-continued

| Example | Cyclic Anhydride | Product | Solvent (mL) | Catalyst (mol %) | Temper (° C.) | Hour | Yield (%) | % ee |
|---|---|---|---|---|---|---|---|---|
| 29 | 1c | 2c | Et$_2$O (5 mL) | Q-BTBSA (5 mol %) | 20 | 4.5 | 90 | 96 |
| 30 | 1d | 2d | Et$_2$O (5 mL) | Q-BTBSA (5 mol %) | 20 | 5 | 90 | 94 |
| 31 | 1d | 2d | IPr$_2$O (10 mL) | Q-BTBSA (5 mol %) | 20 | 5 | 90 | 97.5 |
| 32 | 1e | 2e | Et$_2$O (5 mL) | Q-BTBSA (5 mol %) | 20 | 6 | 88 | 95 |
| 33 | 1f | 2f | MTBE (20 mL) | Q-BTBSA (5 mol %) | −20 | 5 | 95 | 98 |
| 34 | 1f | 2f | IPr$_2$O (50 mL) | Q-BTBSA (5 mol %) | −20 | 9 | 99 | 99 |
| 35 | 1g | 2g | MTBE (5 mL) | Q-BTBSA (10 mol %) | −20 | 4 | 95 | 91 |

TABLE 1-continued

| Example | Cyclic Anhydride | Product | Solvent (mL) | Catalyst (mol %) | Temper (° C.) | Hour | Yield (%) | % ee |
|---|---|---|---|---|---|---|---|---|
| 36 | 1g | 2g | IPr$_2$O (10 mL) | Q-BTBSA (5 mol %) | −20 | 5 | 95 | 87 |
| 37 | 1h | 2h | MTBE (15 mL) | Q-BTBSA (10 mol %) | −20 | 4 | 97 | 94 |
| 38 | 1i | 2i (R = TBDPS) | MtBE (10 mL) | Q-BTBSA (10 mol %) | 20 | 4 | 97 | 92 |
| 39 | 1i | 2i (R = TBDPS) | MTBE (10 mL) | HQ-BTBSA (10 mol %) | 20 | 4 | 96 | 92 |
| 40 | 1i | 2i (R = TBDPS) | MTBE (10 mL) | CD-BTBSA (10 mol %) | 20 | 4 | 94 | 93 |
| 41 | 1i | 2i (R = TBDPS) | MTBE (10 mL) | HCD-BTBSA (10 mol %) | 20 | 3 | 94 | 92 |
| 42 | 1i | 2i (R = TBDPS) | MTBE (10 mL) | Q-PTSA (10 mol %) | 20 | 8 | 89 | 91 |

TABLE 1-continued

| Example | Cyclic Anhydride | Product | Solvent (mL) | Catalyst (mol %) | Temper (°C.) | Hour | Yield (%) | % ee |
|---|---|---|---|---|---|---|---|---|
| 43 | 1i | 2i, R = TBDPS | MTBE (10 mL) | Q-OTSA (10 mol %) | 20 | 8 | 96 | 90 |
| 44 | 1i | 2i, R = TBDPS | MTBE (10 mL) | Q-MTSA (10 mol %) | 20 | 8 | 99 | 91 |
| 45 | 1i | 2i, R = TBDPS | MTBE (10 mL) | Q-1-NSA (10 mol %) | 20 | 12 | 92 | 90 |
| 46 | 1i | 2i, R = TBDPS | MTBE (10 mL) | Q-2-NSA (10 mol %) | 20 | 6 | 91 | 91 |
| 47 | 1i | 2i, R = TBDPS | MTBE (10 mL) | Q-BSA (10 mol %) | 20 | 8 | 96 | 91 |
| 48 | 1i | 2i, R = TBDPS | MTBE (10 mL) | Q-MXSA (10 mol %) | 20 | 7 | 87 | 91 |
| 49 | 1i | 2i, R = TBDPS | MTBE (10 mL) | Q-BTBSA (10 mol %) | 0 | 11 | 96 | 95 |

TABLE 1-continued

| Example | Cyclic Anhydride | Product | Solvent (mL) | Catalyst (mol %) | Temper (°C.) | Hour | Yield (%) | % ee |
|---|---|---|---|---|---|---|---|---|
| 50 | 1i (OTBDPS) | 2i (R = TBDPS) | MTBE (10 mL) | Q-BTBSA (10 mol %) | −20 | 28 | 87 | 96 |
| 51 | 1j (OTBDMS) | 2j (R = TBDMS) | MTBE (10 mL) | Q-BTBSA (10 mol %) | 0 | 11 | 97 | 92 |
| 52 | 1j (OTBDMS) | 2j (R = TBDMS) | MTBE (10 mL) | Q-BTBSA (10 mol %) | −20 | 28 | 98 | 93 |
| 53 | 1k | 2k | MTBE (10 mL) | Q-BTBSA (10 mol %) | 0 | 6 | 95 | 91 |
| 54 | 1k | 2k | MTBE (10 mL) | Q-BTBSA (10 mol %) | −20 | 14 | 96 | 92 |
| 55 | 1l | 2l | MTBE (10 mL) | Q-BTBSA (10 mol %) | 20 | 1 | 92 | 91 |

TABLE 1-continued

| Example | Cyclic Anhydride | Product | Solvent (mL) | Catalyst (mol %) | Temper (° C.) | Hour | Yield (%) | % ee |
|---|---|---|---|---|---|---|---|---|
| 56 | 1l (4-F-C6H4 glutaric anhydride) | 2l (HO2C-CH2-CH(Ar)-CH2-CO2Me, Ar=4-F-C6H4) | MTBE (10 mL) | Q-BTBSA (10 mol %) | −20 | 19 | 81 | 93 |
| 57 | 1m (4-Cl-C6H4 glutaric anhydride) | 2m | MTBE (10 mL) | Q-BTBSA (10 mol %) | 20 | 1 | 92 | 92 |
| 58 | 1m | 2m | MTBE (10 mL) | Q-BTBSA (10 mol %) | −20 | 18 | 87 | 92 |
| 59 | 1n (3,4-di-Cl-C6H3 glutaric anhydride) | 2n | MTBE (10 mL) | Q-BTBSA (10 mol %) | −20 | 19 | 91 | 92 |
| 60 | 1i (OTBDPS glutaric anhydride) | 2o (RO-CH(CH2CO2Allyl)(CH2CO2H), R=TBDPS) | MTBE (10 mL) | Q-BTBSA (10 mol %) | 20 | 20 | 92 | 91 |

TABLE 1-continued

| Example | Cyclic Anhydride | Product | Solvent (mL) | Catalyst (mol %) | Temper (°C.) | Hour | Yield (%) | % ee |
|---|---|---|---|---|---|---|---|---|
| 61 | OTBDPS <br> 1i | RO with CO$_2$Bn and CO$_2$H <br> R = TBDPS <br> 2p | MTBE (10 mL) | Q-BTBSA (10 mol %) | 20 | 8 | 90 | 96 |
| 62 | OTBDPS <br> 1i | RO with CO$_2$Bn and CO$_2$H <br> R = TBDPS <br> 2p | MTBE (10 mL) | Q-BTBSA (10 mol %) | 0 | 15 | 98 | 97 |
| 63 | OTBDPS <br> 1i | RO with CO$_2$Bn and CO$_2$H <br> R = TBDPS <br> 2p | MTBE (10 mL) | Q-BTBSA (10 mol %) | −20 | 4.5d | 93 | 98 |

INDUSTRIAL APPLICABILITY

The derivatized bifunctional cinchona alkaloid catalyst of the present invention may be synthesized from quinine, quinidine, hydroquinine or hydroquinidine, which is easily obtainable from natural products, and has low toxicity and is chemically stable, other than metal catalysts, so that it has high industrial usefulness. In addition, it can proceed for the reaction to be performed in the atmosphere, has high enantioselectivity even at normal temperature, not at high or low temperature, and can be easily recovered after the reaction and reused. Furthermore, using said catalysts, chiral hemiesters having various structures may be synthesized within a short time so as to have high enantioselectivity.

The invention claimed is:

1. A cinchona-based bifunctional organocatalyst comprising a compound of Formula 1 or 2 or a salt thereof:

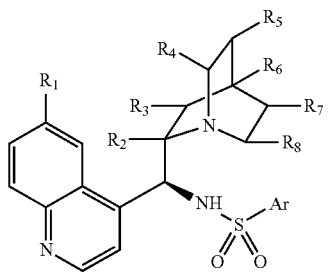

[Formula 1]

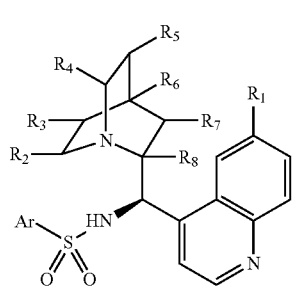

[Formula 2]

wherein, $R_1$ represents hydrogen, an alkyl having 1 to 12 carbons, an alkenyl having 2 to 12 carbons, an alkynyl having 2 to 12 carbons, an alkoxy having 1 to 12 carbons, or an aryl having 6 to 11 member ring, $R_2$, $R_3$, $R_4$, $R_6$, $R_7$ and $R_8$ represent hydrogen, $R_5$ represents an alkyl having 1 to 12 carbons, an alkenyl having 2 to 12 carbons, an alkynyl having 2 to 12 carbons, an alkoxy having 1 to 12 carbons or an aryl having 4 to 11 member ring, and Ar represents an alkyl having 1 to 12 carbons, an alkenyl having 2 to 12 carbons, a cycloalkyl having 3 to 10 carbons, or an aryl having 4 to 11 member ring unsubstituted or substituted with one or more substituents selected from the group consisting of halogen, amino, an aryl having 6 to 10 member ring, an alkyl having 1 to 3 carbons, unsubstituted or substituted with halogen, an alkenyl having 2 to 6 carbons, unsubstituted or substituted with halogen, and an alkoxy having 1 to 6 carbons, unsubstituted or substituted with halogen, with the proviso that Ar is not para-toluene;

wherein, $R_1$ represents hydrogen, an alkyl having 1 to 12 carbons, an alkenyl having 2 to 12 carbons, an alkynyl having 2 to 12 carbons, an alkoxy having 1 to 12 carbons, or an aryl having 6 to 11 member ring, $R_2$, $R_4$, $R_5$, $R_6$, $R_7$ and $R_8$ represent hydrogen, R₃ represents an alkyl having 1 to 12 carbons, an alkenyl having 2 to 12 carbons, an alkynyl having 2 to 12 carbons, an alkoxy having 1 to 12 carbons or an aryl having 4 to 11 member ring, and Ar represents an alkyl having 1 to 12 carbons, an alkenyl having 2 to 12 carbons, a cycloalkyl having 3 to 10 carbons, or an aryl having 4 to 11 member ring unsubstituted or substituted with one or more substituents selected from the group consisting of halogen, amino, an aryl having 6 to 10 member ring, an alkyl having 1 to 3 carbons, unsubstituted or substituted with halogen, an alkenyl having 2 to 6 carbons, unsubstituted or substituted with halogen, and an alkoxy having 1 to 6 carbons, unsubstituted or substituted with halogen, with the proviso that Ar is not para-toluene.

2. The cinchona-based bifunctional organocatalyst of claim 1, characterized in that Ar represents an aryl, having 6 to 10 member ring, unsubstituted or substituted with one or more substituents selected from the group consisting of halogen, amino, an aryl having 6 to 10 member ring, an alkyl having 1 to 3 carbons, unsubstituted or substituted with halogen, an alkenyl having 2 to 6 carbons, unsubstituted or substituted with halogen, and an alkoxy having 1 to 6 carbons, unsubstituted or substituted with halogen, with the proviso that Ar is not para-toluene, and R₁ represents hydrogen, an alkyl having 1 to 6 carbons, an alkenyl having 2 to 6 carbons, an alkynyl having 2 to 6 carbons, or an alkoxy having 1 to 6 carbons, R₂, R₄, R₆, R₇ and R₈ represent hydrogen, and wherein in Formula 1, R₅ represents an alkyl having 1 to 12 carbons, an alkenyl having 2 to 12 carbons, an alkynyl having 2 to 12 carbons, an alkoxy having 1 to 12 carbons or an aryl having 4 to 11 member ring and R₃ is hydrogen, and wherein in Formula 2, R₃ represents an alkyl having 1 to 12 carbons, an alkenyl having 2 to 12 carbons, an alkynyl having 2 to 12 carbons, an alkoxy having 1 to 12 carbons or an aryl having 4 to 11 member ring and R₅ is hydrogen.

3. The cinchona-based bifunctional organocatalyst of claim 1, characterized in that Ar represents a phenyl group or a naphthyl group unsubstituted or substituted with one or more substituents selected from the group consisting of halogen, an alkyl, having 1 to 3 carbons, unsubstituted or substituted with halogen, an alkenyl, having 2 to 4 carbons, unsubstituted or substituted with halogen, and an alkoxy, having 1 to 4 carbons, unsubstituted or substituted with halogen, with the proviso that Ar is not para-toluene.

4. The cinchona-based bifunctional organocatalyst of claim 1, characterized in that R₁ represents hydrogen or an alkoxy having 1 to 4 carbons.

5. The cinchona-based bifunctional organocatalyst of claim 1, characterized in that in the compound of Formula 1, R₃ represents hydrogen, and R₅ represents an alkyl having 1 to 4 carbons or an alkenyl having 2 to 4 carbons.

6. The cinchona-based bifunctional organocatalyst of claim 1, characterized in that in the compound of Formula 2, R₅ represents hydrogen, and R₃ represents an alkyl having 1 to 4 carbons or an alkenyl having 2 to 4 carbons.

7. The cinchona-based bifunctional organocatalyst of claim 1, characterized in that the compound of Formula 1 or 2 is a compound of Formula 1b or 2b, respectively:

[Formula 1b]

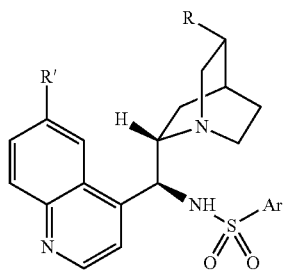

[Formula 2b]

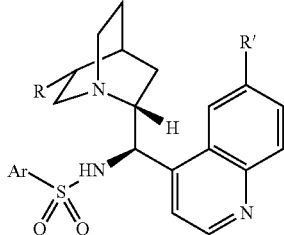

wherein,

R represents ethyl or —CH=CH₂;

R' represents H or —OCH₃; and

Ar represents an aryl group having 6 to 10 member ring unsubstituted or substituted with one or more substituents selected from the group consisting of halogen, amino, an aryl having 6 to 10 member ring, an alkyl having 1 to 3 carbons, unsubstituted or substituted with halogen, an alkenyl having 2 to 6 carbons, unsubstituted or substituted with halogen, and an alkoxy having 1 to 6 carbons, unsubstituted or substituted with halogen, with the proviso that Ar is not para-toluene.

8. The cinchona-based bifunctional organocatalyst of claim 7, characterized in that Ar is selected from the group consisting of 3,5-bis(trifluoromethyl)benzene, ortho-toluene, meta-toluene, para-vinylbenzene, 1-naphthalene, 2-naphthalene, dimethylbenzene and phenyl.

9. A method for preparing a chiral hemiester comprising a step of reacting a prochiral compound or a meso-cyclic acid anhydride with a nucleophile in the presence of a cinchona-based bifunctional organocatalyst comprising a compound of Formula 1 or 2 or a salt thereof according to claim 1.

10. The Method of claim 9, characterized in that

Ar represents an aryl, having 6 to 10 member ring, unsubstituted or substituted with one or more substituents selected from the group consisting of halogen, amino, an aryl having 6 to 10 member ring, an alkyl having 1 to 3 carbons, unsubstituted or substituted with halogen, an alkenyl having 2 to 6 carbons, unsubstituted or substituted with halogen, and an alkoxy having 1 to 6 carbons, unsubstituted or substituted with halogen, with the proviso that Ar is not para-toluene, and R₁ represents hydrogen, an alkyl having 1 to 6 carbons, an alkenyl having 2 to 6 carbons, an alkynyl having 2 to 6 carbons, or an alkoxy having 1 to 6 carbons, R₂, R₄, R₆, R₇ and R₈ represent hydrogen, and wherein in Formula 1, R₅ represents an alkyl having 1 to 12 carbons, an alkenyl having 2 to 12 carbons, an alkynyl having 2 to 12 carbons, an alkoxy having 1 to 12 carbons or an aryl having 4 to 11 member ring and R₃ is hydrogen, and wherein in Formula 2, $R_3$ represents an alkyl having 1 to 12 carbons, an alkenyl having 2 to 12 carbons, an alkynyl having 2 to 12 carbons, an alkoxy having 1 to 12 carbons or an aryl having 4 to 11 member ring and $R_5$ is hydrogen.

11. The Method of claim 9, characterized in that

Ar represents a phenyl group or a naphthyl group unsubstituted or substituted with one or more substitutents selected from the group consisting of halogen, an alkyl, having 1 to 3 carbons, unsubstituted or substituted with halogen, an alkenyl, having 2 to 4 carbons, unsubstituted or substituted with halogen, and an alkoxy, having 1 to 4 carbons, unsubstituted or substituted with halogen, with the proviso that Ar is not para-toluene.

12. The Method of claim 9, characterized in that the compound of Formula 1 or 2 is a compound of Formula 1b or 2b:

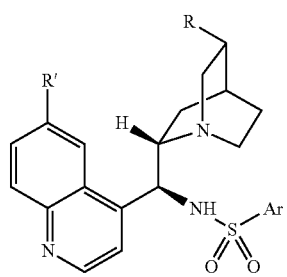

[Formula 1b]

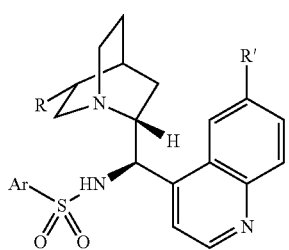

[Formula 2b]

wherein,

R represents ethyl or —CH=CH$_2$;

R' represents H or —OCH$_3$; and

Ar represents an aryl group having 6 to 10 member ring unsubstituted or substituted with one or more substituents selected from the group consisting of halogen, amino, an aryl having 6 to 10 member ring, an alkyl having 1 to 3 carbons, unsubstituted or substituted with halogen, an alkenyl having 2 to 6 carbons, unsubstituted or substituted with halogen, and an alkoxy having 1 to 6 carbons, unsubstituted or substituted with halogen, with the proviso that Ar is not para-toluene.

13. The method of claim 9, characterized in that the nucleophile is alcohol, thiol or amine.

14. The method of claim 9, characterized in that the prochiral compound or meso-cyclic acid anhydride is a cyclic acid anhydride, a substituted succinic acid anhydride or a substituted glutaric acid anhydride.

15. The method of claim 9, characterized in that the nucleophile is used in an amount of 1 to 20 equivalents, based on the prochiral compound or meso-cyclic acid anhydride.

16. The method of claim 9, characterized in that the compound of Formula I is used in an amount of 0.1 to 30 mol %, based on the prochiral compound or meso-cyclic acid anhydride.

17. The method of claim 9, characterized in that the reaction is performed in the presence of an aprotic solvent.

18. A method for preparing a compound of Formula 1 or 2 according to claim 1 comprising a step of reacting an amine of Formula 3a or 4a below with a sulfonyl derivative of Formula 5:

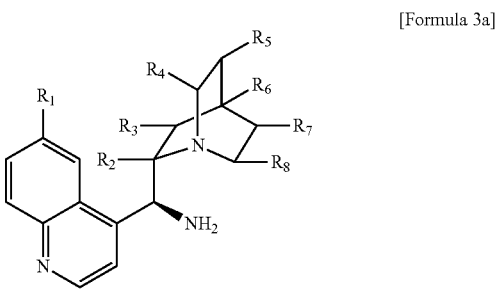

[Formula 3a]

$R_1$ represents hydrogen, an alkyl having 1 to 12 carbons, an alkenyl having 2 to 12 carbons, an alkynyl having 2 to 12 carbons, an alkoxy having 1 to 12 carbons, or an aryl having 6 to 11 member ring, $R_2$, $R_3$, $R_4$, $R_6$, $R_7$ and $R_8$ represent hydrogen, and $R_5$ represent an alkyl having 1 to 12 carbons, an alkenyl having 2 to 12 carbons, an alkynyl having 2 to 12 carbons, an alkoxy having 1 to 12 carbons or an aryl having 4 to 11 member ring,

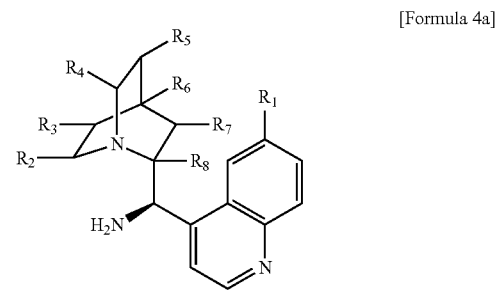

[Formula 4a]

wherein, $R_1$ represents hydrogen, an alkyl having 1 to 12 carbons, an alkenyl having 2 to 12 carbons, an alkynyl having 2 to 12 carbons, an alkoxy having 1 to 12 carbons, or an aryl having 6 to 11 member ring, $R_2$, $R_4$, $R_5$, $R_6$, $R_7$ and $R_8$ represent hydrogen, and $R_3$ represent an alkyl having 1 to 12 carbons, an alkenyl having 2 to 12 carbons, an alkynyl having 2 to 12 carbons, an alkoxy having 1 to 12 carbons or an aryl having 4 to 11 member ring,

[Formula 5]

wherein, $R_2$, $R_4$, $R_6$, $R_7$ and $R_8$ represent hydrogen,

One of $R_3$ and $R_5$ represents an alkyl having 1 to 12 carbons, an alkenyl having 2 to 12 carbons, an alkynyl having 2 to 12 carbons, an alkoxy having 1 to 12 carbons or an aryl having 4 to 11 member ring and the other one is hydrogen, Y represents an alkyl having 1 to 12 carbons, an alkenyl having 2 to 12 carbons, a cycloalkyl having 3 to 10 carbons, or an aryl having 4 to 11 member ring unsubstituted or substituted with one or more substituents selected from the group consisting of halogen, amino, an aryl having 6 to 10 member ring, an alkyl having 1 to 3 carbons, unsubstituted or substituted with halogen, an alkenyl having 2 to 6 carbons, unsubstituted or substituted with halogen, and an alkoxy having 1 to 6 carbons, unsubstituted or substituted with halogen, with the proviso that Y is not para-toluene, and Z represents a halogen atom.

19. The method of claim 18, characterized in that

Y represents an aryl having 6 to 10 member ring unsubstituted or substituted with one or more substituents selected from the group consisting of halogen, amino, an aryl having 6 to 10 member ring, an alkyl, having 1 to 3 carbons, unsubstituted or substituted with halogen, an alkenyl, having 2 to 6 carbons, unsubstituted or substituted with halogen, and an alkoxy, having 1 to 6 carbons, unsubstituted or substituted with halogen, with the proviso that Y is not para-toluene.

20. A cinchona-based bifunctional organocatalyst which is selected from the group consisting of:

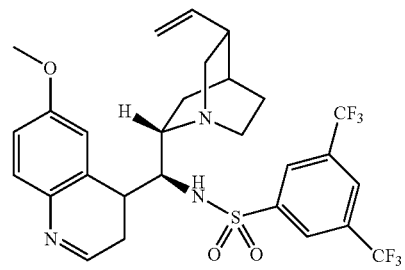

Q-BTBSA

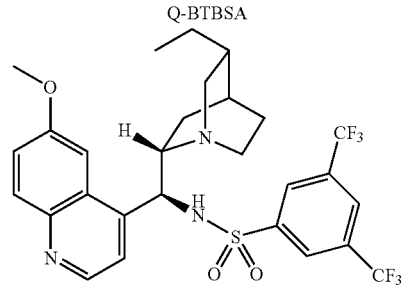

HQ-BTBSA

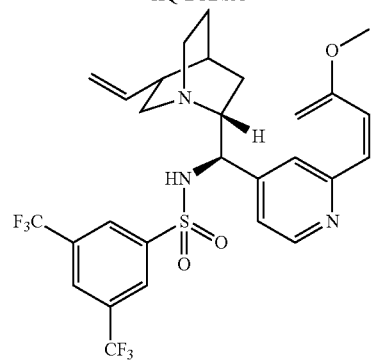

QD-BTBSA

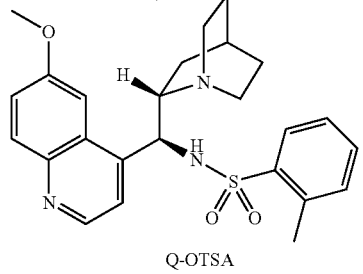

Q-OTSA

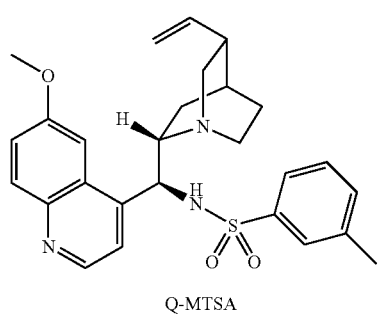

Q-MTSA

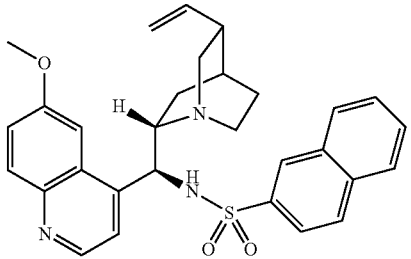

Q-2-NSA

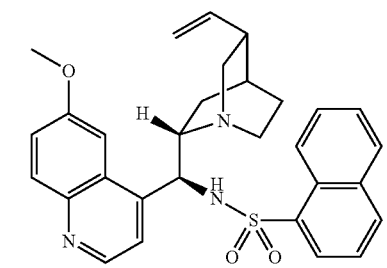

Q-1-NSA

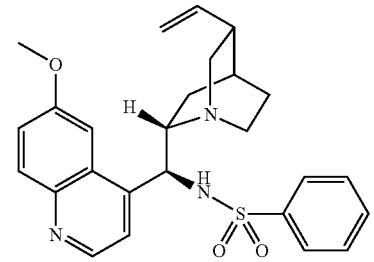

Q-BSA

-continued
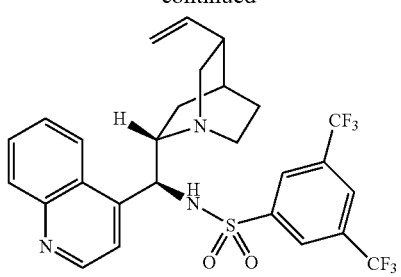
CD-BTBSA
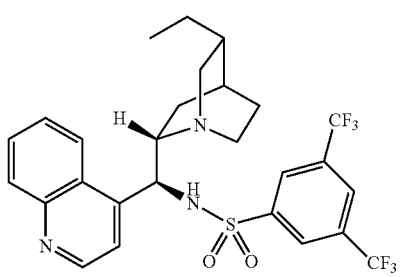
HCD-BTBSA
-continued
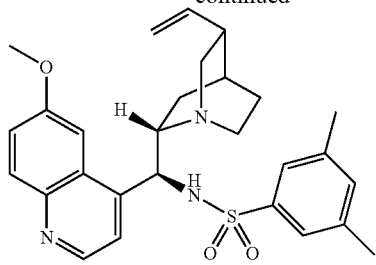
Q-MXSA and
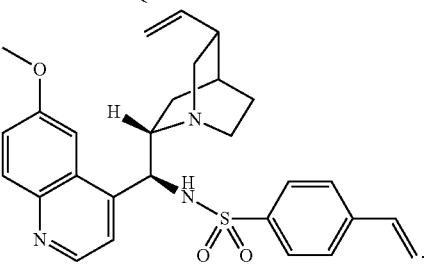
Q-4-VBSA.
* * * * *